United States Patent
Jørgensen et al.

[11] Patent Number: 5,916,796
[45] Date of Patent: Jun. 29, 1999

[54] ENZYME EXHIBITING CELLULASE ACTIVITY

[75] Inventors: Per Linå Jørgensen; Martin Schülein; Christian Hansen, all of Copenhagen, Denmark

[73] Assignee: Novo Nordisk A/S, Bagsvaerd, Denmark

[21] Appl. No.: 07/862,588

[22] PCT Filed: Jan. 18, 1991

[86] PCT No.: PCT/DK91/00013

§ 371 Date: Jul. 27, 1992

§ 102(e) Date: Jul. 27, 1992

[87] PCT Pub. No.: WO91/10732

PCT Pub. Date: Jul. 25, 1991

[30] Foreign Application Priority Data

Jan. 19, 1990 [DK] Denmark .................................. 0164/90

[51] Int. Cl.⁶ .............................. C12N 9/42; C12N 15/56; C12S 11/00; C11D 3/386
[52] U.S. Cl. ................... 435/209; 435/69.1; 435/252.31; 435/320.1; 435/263; 536/23.2; 252/174.12; 935/14; 935/29; 935/74
[58] Field of Search ................................ 435/69.1, 252.3, 435/252.31, 252.33, 209, 263, 320.1; 530/350; 536/23.2, 23.7; 252/174.12

[56] References Cited

U.S. PATENT DOCUMENTS

| | | | |
|---|---|---|---|
| 4,443,355 | 4/1984 | Murata et al. | 252/174.12 |
| 4,652,639 | 3/1987 | Stabinsky | 435/91.52 |
| 4,822,516 | 4/1989 | Suzuki et al. | 252/174.12 |
| 5,006,126 | 4/1991 | Olsen et al. | 8/401 |
| 5,010,000 | 4/1991 | Palva | 435/69.1 |

FOREIGN PATENT DOCUMENTS

| | | |
|---|---|---|
| 0 265 832 | 5/1988 | European Pat. Off. . |
| 0 269 977 | 6/1988 | European Pat. Off. . |
| 0 270 974 | 6/1988 | European Pat. Off. . |
| 0 271 004 | 6/1988 | European Pat. Off. . |
| 62232386 | 10/1987 | Japan . |
| WO 89/09259 | 10/1989 | WIPO . |
| 92003557 | 3/1992 | WIPO .................................. 435/69.1 |

OTHER PUBLICATIONS

Fortkamp, E., et al., DNA, vol. 5, "Cloning and expression in *Escherichia coli* of a synthetic DNA for hirudin, the blood coagulation inhibitor in the leech", pp. 511–517, 1986.

Warren et al., Chem. Abs., vol. 108, No. 19, p. 295, abs. No. 163739k (1988).

Greenwood et al., Chem. Abs., vol. 110, No. 23, abs. No. 208834x (1989).

Kilburn et al., Chem. Abs., vol. 111, No. 19, p. 331, abs. No. 170011g (1989).

Ong et al., Chem. Abs., vol. 111, No. 21, p. 619, abs. No. 192974a (1989).

Borriss, R., et al., Carlsberg Research Communications, vol. 54, No. 2, pp. 41–54, 1989.

Fukumori, F., et al., Journal of General Microbiology, vol. 131, Part 12, pp. 3339–3345, Dec., 1985.

MacKay, R.M., et al., Nucleic Acids Research, vol. 14, No. 22, pp. 9159–9170, 1986.

(List continued on next page.)

*Primary Examiner*—Robert A. Wax
*Assistant Examiner*—William W. Moore
*Attorney, Agent, or Firm*—Steve T. Zelson, Esq.; Elias J. Lambiris, Esq.

[57] ABSTRACT

This invention relates to an enzyme which exhibits cellulase activity and is producible by a strain of Bacillus sp., NCIMB 40250, or a related Bacillus sp. strain, or a derivative of said cellulase. This invention also relates to an enzyme which comprises a core region derived from an endoglucanase combined with a cellulose-binding domain derived from another cellulase, or which comprises a core region derived from another cellulase combined with a cellulose-binding domain derived from an endoglucanase.

35 Claims, 13 Drawing Sheets

OTHER PUBLICATIONS

Park, S.H., et al., Agricultural and Biological Chemistry, vol. 55, No. 2, pp. 441–448, Feb., 1991.

Kim, J–M, et al., Applied and Environmental Microbiology, vol. 53, No. 11, pp. 2656–2659, Nov., 1987.

Hansen, C.K., et al., Journal of Bacteriology, vol. 174, No. 11, pp. 3522–3531, Jun., 1992.

Jøorgensen, P.L., et al., Gene, vol. 93, pp. 55–60, Sep., 1990.

Ong, E., et al., Tibtech, vol. 7, pp. 239–243, Sep., 1989.

Zayre et al. 1988. Applied and Environmental Microbiology 54 (5) : 1289–1292.

Van der Plas et al. 1989. Moleculer Microbiology 3(3) : 275–284.

Suggs et al. 1981. Proc. Natl. Acad. Sci., USA, 78(11) : 6613–6617.

Nakamura. 1984. Int. J. Syst. Bacteriol. 34 (2) : 224–226.

Saul et al. 1989. Nucleic Acid Res. 17 (1) : 439.

Beguir et al. 1985. J. Bacteriol. 162 (1) : 102–105.

Hall et al. 1988. Gene 69 : 29–38.

Day, 1983. *How to Write and Publish a Scientific Paper,* iSi Press, Philadelphia, PA, pp. 15–19.

| PLASMID | INSERT | |
|---|---|---|
| pPL 517 | 2750bp | P Ea B E     P C C     E     B P C     Ea    P<br>ENDO 1 |
| pPL 382 | 2500bp | H Sp E     H E P     H E     EH<br>ENDO 2 |
| pPL 591 | 11000bp | E    H    H    S    S H    H H S    E<br>ENDO 3A |
| pPL 592 | 14000bp | H    E    H    Sa    E Ba    Sa    E    H    Ba    H |

Fig. 1

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 2977 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Bacillus lautus
      (B) STRAIN: NCIMB 40250

(ix) FEATURE:
      (A) NAME/KEY: CDS (B) LOCATION: 677..2776
(D) OTHER INFORMATION:

(xi) SEQUENCE DESCRIPTION: SEQ ID NO:1:

```
ATCTTGAAGC TTCGAGGTTC GCGTAACCAG GTCGATCGGC TGACTTTCCT CGCCAAGCTG      60

CACCATGGCT TCATAGATTA ATTGGTGAGG AGGATCATAG AAATCTTCCG TCCGCACCGC     120

TCCATGGCGG TAATCAGCGC TTCCGACTGC AGTACAGAGC GGCCGATACA AATGCAGCCG     180

ACAACCAGAT CAAGCCGTCC TTCAACATCA AAACAACGG TACTTCGGCT GTTGATTTAA      240

GCACGCTCAA ATCCGCTAC TACTTCACCA AGGATGGTTC TGCGGCGGTG AACGGCTGGA      300

TCGACTGGGC GCAGCTCGGC GGCAGCAACA TTCAGATCTC GTTTGGCAAC CATACTGGCA     360

CGAATTCGGA TACGTACGTG GAGCTGAGCT TCTCGTCCGA GGCAGGCTCG ATTGCGGCGG     420

GCGGCCAATC CGGTGAAATC CAGCTGCGCA TGTCCAAGAC GGACTGGTCG AACTTTAACG     480

AGGCGAACGA CTACTCGTTC GATGGGACGA AGACGGCCTT TGCTGACTGG GATCGGGTCG     540

TATTGTACCA GAACGGCCAA ATAGTGTGGG AACTGCTCC ATAAACCGAT ACAGGGGAAT      600

GTGCCGGAAC CGCTCTTTTG CAGGGCAGAC TGGCGGTATC CCTTGCTGAA ATGACTATTC     660

CTGGGAGGGA TCAAAA ATG AAG ACA AGA CAA AGA AAG CGG CTG TTC GTC         709
                  Met Lys Thr Arg Gln Arg Lys Arg Leu Phe Val
                   1               5                  10

AGT GCG GCG CTG GCA GTA TCC TTG ACA ATG ACC GTA CCG ATG CCC GCT       757
Ser Ala Ala Leu Ala Val Ser Leu Thr Met Thr Val Pro Met Pro Ala
             15                  20                  25

TCT GTA AAT GCA GCT GCG AGT GAT GTC ACT TTC ACG ATT AAT ACG CAG       805
Ser Val Asn Ala Ala Ala Ser Asp Val Thr Phe Thr Ile Asn Thr Gln
         30                  35                  40

TCG GAA CGT GCA GCG ATC AGC CCC AAT ATT TAC GGA ACC AAT CAG GAT       853
Ser Glu Arg Ala Ala Ile Ser Pro Asn Ile Tyr Gly Thr Asn Gln Asp
     45                  50                  55

CTG AGC GGG ACG GAG AAC TGG TCA TCC CGC AGG CTC GGA GGC AAC CGG       901
Leu Ser Gly Thr Glu Asn Trp Ser Ser Arg Arg Leu Gly Gly Asn Arg
 60                  65                  70                  75

CTG ACG GGT TAC AAC TGG GAG AAC AAC GCA TCC AGC GCC GGA AGG GAC       949
Leu Thr Gly Tyr Asn Trp Glu Asn Asn Ala Ser Ser Ala Gly Arg Asp
                 80                  85                  90

TGG CTT CAT TAC AGC GAT GAT TTT CTC TGC GGC AAC GGT GGT GTT CCA       997
Trp Leu His Tyr Ser Asp Asp Phe Leu Cys Gly Asn Gly Gly Val Pro
             95                 100                 105

GAC ACC GAC TGC GAC AAG CCG GGG GCG GTT GTT ACC GCT TTT CAC GAT      1045
Asp Thr Asp Cys Asp Lys Pro Gly Ala Val Val Thr Ala Phe His Asp
         110                 115                 120

AAA TCT TTG GAG AAT GGA GCT TAC TCC ATT GTA ACG CTG CAA ATG GCG      1093
Lys Ser Leu Glu Asn Gly Ala Tyr Ser Ile Val Thr Leu Gln Met Ala
     125                 130                 135

GGT TAT GTG TCC CGG GAT AAG AAC GGT CCA GTT GAC GAG AGT GAG ACG      1141
Gly Tyr Val Ser Arg Asp Lys Asn Gly Pro Val Asp Glu Ser Glu Thr
140                 145                 150                 155

GCT CCG TCA CCG CGT TGG GAT AAG GTC GAG TTT GCC AAA AAT GCG CCG      1189
Ala Pro Ser Pro Arg Trp Asp Lys Val Glu Phe Ala Lys Asn Ala Pro
                 160                 165                 170

TTC TCC CTT CAG CCT GAT CTG AAC GAC GGA CAA GTG TAT ATG GAT GAA      1237
Phe Ser Leu Gln Pro Asp Leu Asn Asp Gly Gln Val Tyr Met Asp Glu
             175                 180                 185

GAA GTT AAC TTC CTG GTC AAC CGG TAT GGA AAC GCT TCA ACG TCA ACG      1285
Glu Val Asn Phe Leu Val Asn Arg Tyr Gly Asn Ala Ser Thr Ser Thr
         190                 195                 200
```

-continued

| | | |
|---|---|---|
| GGC ATC AAA GCG TAT TCG CTG GAT AAC GAG CCG GCG CTG TGG TCT GAG<br>Gly Ile Lys Ala Tyr Ser Leu Asp Asn Glu Pro Ala Leu Trp Ser Glu<br>205                         210                       215 | 1333 |
| ACG CAT CCA AGG ATT CAT CCG GAG CAG TTA CAA GCG GCA GAA CTC GTC<br>Thr His Pro Arg Ile His Pro Glu Gln Leu Gln Ala Ala Glu Leu Val<br>220                         225                       230                   235 | 1381 |
| GCT AAG AGC ATC GAC TTG TCA AAG GCG GTG AAG AAC GTC GAT CCG CAT<br>Ala Lys Ser Ile Asp Leu Ser Lys Ala Val Lys Asn Val Asp Pro His<br>                      240                       245                       250 | 1429 |
| GCC GAA ATA TTC GGT CCT GCC CTT TAC GGT TTC GGC GCA TAT TTG TCT<br>Ala Glu Ile Phe Gly Pro Ala Leu Tyr Gly Phe Gly Ala Tyr Leu Ser<br>                255                       260                       265 | 1477 |
| CTG CAG GAC GCA CCG GAT TGG CCG AGT TTG CAA GGC AAC TAC AGC TGG<br>Leu Gln Asp Ala Pro Asp Trp Pro Ser Leu Gln Gly Asn Tyr Ser Trp<br>           270                       275                       280 | 1525 |
| TTT ATC GAT TAC TAT CTG GAT CAG ATG AAG AAT GCT CAT ACG CAG AAC<br>Phe Ile Asp Tyr Tyr Leu Asp Gln Met Lys Asn Ala His Thr Gln Asn<br>285                         290                       295 | 1573 |
| GGC AAA AGA TTG CTC GAT GTG CTG GAC GTC CAC TGG TAT CCG GAA GCA<br>Gly Lys Arg Leu Leu Asp Val Leu Asp Val His Trp Tyr Pro Glu Ala<br>300                         305                       310                   315 | 1621 |
| CAG GGC GGA GGC CAG CGA ATC GTC TTT GGC GGG GCG GGC AAT ATC GAT<br>Gln Gly Gly Gly Gln Arg Ile Val Phe Gly Gly Ala Gly Asn Ile Asp<br>                      320                       325                       330 | 1669 |
| ACG CAG AAG GCT CGC GTA CAA GCG CCA AGA TCG CTA TGG GAT CCG GCT<br>Thr Gln Lys Ala Arg Val Gln Ala Pro Arg Ser Leu Trp Asp Pro Ala<br>                335                       340                       345 | 1717 |
| TAC CAG GAA GAC AGC TGG ATC GGC ACA TGG TTT TCA AGC TAC TTG CCC<br>Tyr Gln Glu Asp Ser Trp Ile Gly Thr Trp Phe Ser Ser Tyr Leu Pro<br>           350                       355                       360 | 1765 |
| TTA ATT CCG AAG CTG CAA TCT TCG ATT CAG ACG TAT TAT CCG GGT ACG<br>Leu Ile Pro Lys Leu Gln Ser Ser Ile Gln Thr Tyr Tyr Pro Gly Thr<br>365                         370                       375 | 1813 |
| AAG CTG GCG ATC ACA GAG TTC AGC TAC GGC GGA GAC AAT CAC ATT TCG<br>Lys Leu Ala Ile Thr Glu Phe Ser Tyr Gly Gly Asp Asn His Ile Ser<br>380                         385                       390                   395 | 1861 |
| GGA GGC ATA GCT ACC GCG GAC GCG CTC GGC ATT TTT GGA AAA TAT GGC<br>Gly Gly Ile Ala Thr Ala Asp Ala Leu Gly Ile Phe Gly Lys Tyr Gly<br>                      400                       405                       410 | 1909 |
| GTT TAT GCC GCG AAT TAC TGG CAG ACG GAG GAC AAT ACC GAT TAT ACC<br>Val Tyr Ala Ala Asn Tyr Trp Gln Thr Glu Asp Asn Thr Asp Tyr Thr<br>                415                       420                       425 | 1957 |
| AGC GCT GCT TAC AAG CTG TAT CGC AAC TAC GAC GGC AAT AAA TCG GGG<br>Ser Ala Ala Tyr Lys Leu Tyr Arg Asn Tyr Asp Gly Asn Lys Ser Gly<br>           430                       435                       440 | 2005 |
| TTC GGC TCG ATC AAA GTG GAC GCC GCT ACG TCC GAT ACG GAG AAC AGC<br>Phe Gly Ser Ile Lys Val Asp Ala Ala Thr Ser Asp Thr Glu Asn Ser<br>445                         450                       455 | 2053 |
| TCG GTA TAC GCT TCG GTA ACT GAC GAG GAG AAT TCC GAA CTC CAC CTG<br>Ser Val Tyr Ala Ser Val Thr Asp Glu Glu Asn Ser Glu Leu His Leu<br>460                         465                       470                   475 | 2101 |
| ATC GTG CTG AAT AAA AAT TTC GAT GAT CCG ATC AAC GCT ACT TTC CAG<br>Ile Val Leu Asn Lys Asn Phe Asp Asp Pro Ile Asn Ala Thr Phe Gln<br>                      480                       485                   490 | 2149 |
| CTG TCT GGT GAT AAA ACC TAC ACA TCC GGG AGA GTA TGG GGC TTC GAC<br>Leu Ser Gly Asp Lys Thr Tyr Thr Ser Gly Arg Val Trp Gly Phe Asp<br>           495                       500                       505 | 2197 |
| CAA ACC GGA TCC GAC ATT ACG GAA CAA GCA GCT ATA ACG AAT ATT AAC<br>Gln Thr Gly Ser Asp Ile Thr Glu Gln Ala Ala Ile Thr Asn Ile Asn<br>510                         515                       520 | 2245 |

```
AAC AAT CAA TTC ACG TAT ACG CTT CCT CCA TTG TCG GCT TAC CAC ATT         2293
Asn Asn Gln Phe Thr Tyr Thr Leu Pro Pro Leu Ser Ala Tyr His Ile
        525                 530                 535

GTT CTG AAA GCG GAT AGC ACC GAA CCG GTC AAC TCC GAT CTC GTC GTG         2341
Val Leu Lys Ala Asp Ser Thr Glu Pro Val Asn Ser Asp Leu Val Val
540                 545                 550                 555

CAG TAT AAG GAC GGT GAT CGC AAC AAT GCA ACC GAC AAT CAG ATC AAG         2389
Gln Tyr Lys Asp Gly Asp Arg Asn Asn Ala Thr Asp Asn Gln Ile Lys
                560                 565                 570

CCG CAT TTC AAT ATT CAA AAT AAA GGG ACC AGC CCG GTA GAT CTG AGT         2437
Pro His Phe Asn Ile Gln Asn Lys Gly Thr Ser Pro Val Asp Leu Ser
                    575                 580                 585

TCC CTT ACC CTG CGC TAC TAT TTT ACC AAA GAC AGC TCT GCA GCG ATG         2485
Ser Leu Thr Leu Arg Tyr Tyr Phe Thr Lys Asp Ser Ser Ala Ala Met
        590                 595                 600

AAC GGC TGG ATC GAT TGG GCG AAG CTC GGC GGC AGC AAC ATT CAG ATT         2533
Asn Gly Trp Ile Asp Trp Ala Lys Leu Gly Gly Ser Asn Ile Gln Ile
605                 610                 615

TCG TTC GGT AAT CAT AAT GGC GCG GAT TCG GAT ACG TAC GCG GAG CTG         2581
Ser Phe Gly Asn His Asn Gly Ala Asp Ser Asp Thr Tyr Ala Glu Leu
620                 625                 630                 635

GGC TTC TCG TCC GGC GCA GGC TCG ATT GCG GAG GGC GGT CAA TCC GGC         2629
Gly Phe Ser Ser Gly Ala Gly Ser Ile Ala Glu Gly Gly Gln Ser Gly
                640                 645                 650

GAA ATC CAG CTG CGC ATG TCG AAG GCG GAC TGG TCG AAC TTC AAC GAG         2677
Glu Ile Gln Leu Arg Met Ser Lys Ala Asp Trp Ser Asn Phe Asn Glu
                    655                 660                 665

GCG AAC GAC TAC TCG TTC GAT GGG GCG AAG ACG GCC TAT ATA GAT TGG         2725
Ala Asn Asp Tyr Ser Phe Asp Gly Ala Lys Thr Ala Tyr Ile Asp Trp
        670                 675                 680

GAT CGC GTG ACG CTA TAC CAA GAC GGA CAA CTC GTA TGG GGA ATC GAG         2773
Asp Arg Val Thr Leu Tyr Gln Asp Gly Gln Leu Val Trp Gly Ile Glu
685                 690                 695

CCG TAGAAGATGA CTAGACAACA TTAGTGATGA GACGCGGCCG GCCATAACGG              2826
Pro
700

CTGTCTTGAC TCTGATTCGA TCAAAAAATC AAAGCAAAGG GGATGAAAGT AATGAATGTT       2886

GCGATTCAAA AGAGAATCGG ATCAATATTG ATGATTGCCT CACTAATTAT TAGCTTATTG       2946

CCGTTAGGGA GCAGCAGAAC GTATGCTGCA G                                      2977

(2) INFORMATION FOR SEQ ID NO:2:

(i) SEQUENCE CHARACTERISTICS:
        (A) LENGTH: 700 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Thr Arg Gln Arg Lys Arg Leu Phe Val Ser Ala Ala Leu Ala
1               5                   10                  15

Val Ser Leu Thr Met Thr Val Pro Met Pro Ala Ser Val Asn Ala Ala
            20                  25                  30

Ala Ser Asp Val Thr Phe Thr Ile Asn Thr Gln Ser Glu Arg Ala Ala
        35                  40                  45

Ile Ser Pro Asn Ile Tyr Gly Thr Asn Gln Asp Leu Ser Gly Thr Glu
    50                  55                  60

Asn Trp Ser Ser Arg Arg Leu Gly Gly Asn Arg Leu Thr Gly Tyr Asn
65                  70                  75                  80
```

```
Trp Glu Asn Asn Ala Ser Ser Ala Gly Arg Asp Trp Leu His Tyr Ser
                85                  90                  95

Asp Asp Phe Leu Cys Gly Asn Gly Val Pro Asp Thr Asp Cys Asp
            100                 105                 110

Lys Pro Gly Ala Val Val Thr Ala Phe His Asp Lys Ser Leu Glu Asn
            115                 120                 125

Gly Ala Tyr Ser Ile Val Thr Leu Gln Met Ala Gly Tyr Val Ser Arg
130                 135                 140

Asp Lys Asn Gly Pro Val Asp Glu Ser Glu Thr Ala Pro Ser Pro Arg
145                 150                 155                 160

Trp Asp Lys Val Glu Phe Ala Lys Asn Ala Pro Phe Ser Leu Gln Pro
                165                 170                 175

Asp Leu Asn Asp Gly Gln Val Tyr Met Asp Glu Val Asn Phe Leu
            180                 185                 190

Val Asn Arg Tyr Gly Asn Ala Ser Thr Ser Thr Gly Ile Lys Ala Tyr
            195                 200                 205

Ser Leu Asp Asn Glu Pro Ala Leu Trp Ser Glu Thr His Pro Arg Ile
    210                 215                 220

His Pro Glu Gln Leu Gln Ala Ala Glu Leu Val Ala Lys Ser Ile Asp
225                 230                 235                 240

Leu Ser Lys Ala Val Lys Asn Val Asp Pro His Ala Glu Ile Phe Gly
                245                 250                 255

Pro Ala Leu Tyr Gly Phe Gly Ala Tyr Leu Ser Leu Gln Asp Ala Pro
            260                 265                 270

Asp Trp Pro Ser Leu Gln Gly Asn Tyr Ser Trp Phe Ile Asp Tyr Tyr
    275                 280                 285

Leu Asp Gln Met Lys Asn Ala His Thr Gln Asn Gly Lys Arg Leu Leu
    290                 295                 300

Asp Val Leu Asp Val His Trp Tyr Pro Glu Ala Gln Gly Gly Gly Gln
305                 310                 315                 320

Arg Ile Val Phe Gly Gly Ala Gly Asn Ile Asp Thr Gln Lys Ala Arg
                325                 330                 335

Val Gln Ala Pro Arg Ser Leu Trp Asp Pro Ala Tyr Gln Glu Asp Ser
            340                 345                 350

Trp Ile Gly Thr Trp Phe Ser Ser Tyr Leu Pro Leu Ile Pro Lys Leu
            355                 360                 365

Gln Ser Ser Ile Gln Thr Tyr Tyr Pro Gly Thr Lys Leu Ala Ile Thr
    370                 375                 380

Glu Phe Ser Tyr Gly Gly Asp Asn His Ile Ser Gly Gly Ile Ala Thr
385                 390                 395                 400

Ala Asp Ala Leu Gly Ile Phe Gly Lys Tyr Gly Val Tyr Ala Ala Asn
            405                 410                 415

Tyr Trp Gln Thr Glu Asp Asn Thr Asp Tyr Thr Ser Ala Ala Tyr Lys
            420                 425                 430

Leu Tyr Arg Asn Tyr Asp Gly Asn Lys Ser Gly Phe Gly Ser Ile Lys
    435                 440                 445

Val Asp Ala Ala Thr Ser Asp Thr Glu Asn Ser Val Tyr Ala Ser
450                 455                 460

Val Thr Asp Glu Glu Asn Ser Glu Leu His Leu Ile Val Leu Asn Lys
465                 470                 475                 480

Asn Phe Asp Asp Pro Ile Asn Ala Thr Phe Gln Leu Ser Gly Asp Lys
            485                 490                 495
```

```
Thr Tyr Thr Ser Gly Arg Val Trp Gly Phe Asp Gln Thr Gly Ser Asp
            500                 505                 510

Ile Thr Glu Gln Ala Ala Ile Thr Asn Ile Asn Asn Asn Gln Phe Thr
        515                 520                 525

Tyr Thr Leu Pro Pro Leu Ser Ala Tyr His Ile Val Leu Lys Ala Asp
    530                 535                 540

Ser Thr Glu Pro Val Asn Ser Asp Leu Val Val Gln Tyr Lys Asp Gly
545                 550                 555                 560

Asp Arg Asn Asn Ala Thr Asp Asn Gln Ile Lys Pro His Phe Asn Ile
                565                 570                 575

Gln Asn Lys Gly Thr Ser Pro Val Asp Leu Ser Ser Leu Thr Leu Arg
            580                 585                 590

Tyr Tyr Phe Thr Lys Asp Ser Ser Ala Ala Met Asn Gly Trp Ile Asp
        595                 600                 605

Trp Ala Lys Leu Gly Gly Ser Asn Ile Gln Ile Ser Phe Gly Asn His
    610                 615                 620

Asn Gly Ala Asp Ser Asp Thr Tyr Ala Glu Leu Gly Phe Ser Ser Gly
625                 630                 635                 640

Ala Gly Ser Ile Ala Glu Gly Gly Gln Ser Gly Glu Ile Gln Leu Arg
                645                 650                 655

Met Ser Lys Ala Asp Trp Ser Asn Phe Asn Glu Ala Asn Asp Tyr Ser
            660                 665                 670

Phe Asp Gly Ala Lys Thr Ala Tyr Ile Asp Trp Asp Arg Val Thr Leu
        675                 680                 685

Tyr Gln Asp Gly Gln Leu Val Trp Gly Ile Glu Pro
    690                 695                 700

(2) INFORMATION FOR SEQ ID NO:3:

(i) SEQUENCE CHARACTERISTICS:
        (A) LENGTH: 2323 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Bacillus lautus
        (B) STRAIN: NCIMB 40250

(ix) FEATURE:
        (A) NAME/KEY: CDS
        (B) LOCATION: 172..1869
        (D) OTHER INFORMATION:

(xi) SEQUENCE DESCRIPTION: SEQ ID NO:3:

GGGGTTTTGT TCATTTCAAG AAAGAGCACG AATAAACATC GCTAATTTAC ACATGATTTA      60

TTCTCTAATT ATTATGGTGC ATGCCAATTG GAAAATGTAG TAGATTAGTC ATCGTAACCT     120

GCTTTCATGC CAAGATATGT AATTTTTAAA AAAGAGTAAA GGAGAATTCA G ATG AAA     177
                                                        Met Lys
                                                          1

AAA CGT AGA AGC AGT AAA GTT ATT CTT TCG TTG GCC ATC GTT GTT GCA      225
Lys Arg Arg Ser Ser Lys Val Ile Leu Ser Leu Ala Ile Val Val Ala
        5                  10                  15

TTA TTG GCA GCC GTC GAA CCT AAT GCC GCT TTA GCA GCG GCT CCA CCA      273
Leu Leu Ala Ala Val Glu Pro Asn Ala Ala Leu Ala Ala Ala Pro Pro
    20                  25                  30

AGT GCC ATG CAG TCC TAT GTT GAA GCG ATG CAG CCT GGC TGG AAC CTT      321
Ser Ala Met Gln Ser Tyr Val Glu Ala Met Gln Pro Gly Trp Asn Leu
35                  40                  45                  50
```

```
GGC AAT TCT CTG GAT GCT GTC GGT GCG GAT GAG ACG CTG GCA CGG GGC     369
Gly Asn Ser Leu Asp Ala Val Gly Ala Asp Glu Thr Leu Ala Arg Gly
                55                  60                  65

AAT CCG CGG ATC ACG AAA GAG CTC ATT CAG AAC ATC GCT GCG CAA GGC     417
Asn Pro Arg Ile Thr Lys Glu Leu Ile Gln Asn Ile Ala Ala Gln Gly
            70                  75                  80

TAT AAG AGC ATA CGG ATT CCT GTT ACC TGG GAT TCC CAT ATC GGC GCG     465
Tyr Lys Ser Ile Arg Ile Pro Val Thr Trp Asp Ser His Ile Gly Ala
        85                  90                  95

GCC CCA AAT TAT CAA ATT GAA GCT GCG TAC CTC AAT CGA GTG CAG GAG     513
Ala Pro Asn Tyr Gln Ile Glu Ala Ala Tyr Leu Asn Arg Val Gln Glu
    100                 105                 110

GTC GTA CAG TGG GCT TTG GAC GCG AAC CTC TAT GTG ATG ATT AAT GTC     561
Val Val Gln Trp Ala Leu Asp Ala Asn Leu Tyr Val Met Ile Asn Val
115                 120                 125                 130

CAT CAT GAT TCC TGG CTA TGG ATC AGC AAA ATG GAG TCG CAG CAC GAT     609
His His Asp Ser Trp Leu Trp Ile Ser Lys Met Glu Ser Gln His Asp
                135                 140                 145

CAA GTA CTG GCC CGT TAT AAT GCG ATT TGG ACG CAA ATT GCC AAC AAG     657
Gln Val Leu Ala Arg Tyr Asn Ala Ile Trp Thr Gln Ile Ala Asn Lys
            150                 155                 160

TTC AAG AAC AGC CCG AGC AAG CTG ATG TTC GAG AGC GTG AAT GAG CCT     705
Phe Lys Asn Ser Pro Ser Lys Leu Met Phe Glu Ser Val Asn Glu Pro
        165                 170                 175

CGC TTT ACG GAT GGC GGA ACT ACG GAT GAA GCC AAG CAG CAA AAA ATG     753
Arg Phe Thr Asp Gly Gly Thr Thr Asp Glu Ala Lys Gln Gln Lys Met
    180                 185                 190

CTG GAC GAG CTG AAC GTA TCC TTT TTC AAC ATC GTC AGA AAT TCC GGC     801
Leu Asp Glu Leu Asn Val Ser Phe Phe Asn Ile Val Arg Asn Ser Gly
195                 200                 205                 210

GGC CAG AAC GCG ACT CGC CCG CTA GTT CTT TCT ACG TTG GAG GCC TCT     849
Gly Gln Asn Ala Thr Arg Pro Leu Val Leu Ser Thr Leu Glu Ala Ser
                215                 220                 225

CCC ACC CAA GAG AGA ATG ACG GCG CTT TAT AAT ACG ATG ACC AAA CTG     897
Pro Thr Gln Glu Arg Met Thr Ala Leu Tyr Asn Thr Met Thr Lys Leu
            230                 235                 240

AAC GAC AAG AAT CTG ATC GCA ACC GTT CAT TTT TAT GGA TTC TGG CCG     945
Asn Asp Lys Asn Leu Ile Ala Thr Val His Phe Tyr Gly Phe Trp Pro
        245                 250                 255

TTT AGC GTA AAT ATC GCA GGA TAT ACG AAA TTT GAT GCG GAG ACG CAA     993
Phe Ser Val Asn Ile Ala Gly Tyr Thr Lys Phe Asp Ala Glu Thr Gln
    260                 265                 270

AAT GAT ATT ATA ACG ACC TTC GAT AAC GTG TAT AAC ACA TTT GTA GCA    1041
Asn Asp Ile Ile Thr Thr Phe Asp Asn Val Tyr Asn Thr Phe Val Ala
275                 280                 285                 290

AAG GGA ATC CCG GTG GTA GTC GGC GAA TAT GGC CTT CTT GGA TTC GAT    1089
Lys Gly Ile Pro Val Val Val Gly Glu Tyr Gly Leu Leu Gly Phe Asp
                295                 300                 305

AAG AAT ACC GGC GTC ATT GAA CAG GGT GAG AAA TTG AAA TTT TTC GAG    1137
Lys Asn Thr Gly Val Ile Glu Gln Gly Glu Lys Leu Lys Phe Phe Glu
            310                 315                 320

TTT TTT GCC CAG TAT GTG AAG CAA AAA AGC ATT TCC ACT ATG CTA TGG    1185
Phe Phe Ala Gln Tyr Val Lys Gln Lys Ser Ile Ser Thr Met Leu Trp
        325                 330                 335

GAT AAC GGA CAG CAC TTC AAC CGC ACG AGC TTC AAG TGG TCT GAC CCG    1233
Asp Asn Gly Gln His Phe Asn Arg Thr Ser Phe Lys Trp Ser Asp Pro
    340                 345                 350

GAT TTA TTC AAT ATG ATC AAG GCC AGT TGG ACC GGA CGT TCA TCC ACG    1281
Asp Leu Phe Asn Met Ile Lys Ala Ser Trp Thr Gly Arg Ser Ser Thr
355                 360                 365                 370
```

```
GCT TCC AGC GAC CTG ATC CAT GTC AAG CAG GGC ACG GCG GTA AAA GAT      1329
Ala Ser Ser Asp Leu Ile His Val Lys Gln Gly Thr Ala Val Lys Asp
            375                 380                 385

ACT TCG GTT CAG CTC AAT CTT AAC GGG AAT ACG CTA ACT TCC CTT TCC      1377
Thr Ser Val Gln Leu Asn Leu Asn Gly Asn Thr Leu Thr Ser Leu Ser
            390                 395                 400

GTA AAT GGA ACG ACA CTG AAA TCA GGC ACA GAT TAC ACT TTA AAC AGC      1425
Val Asn Gly Thr Thr Leu Lys Ser Gly Thr Asp Tyr Thr Leu Asn Ser
            405                 410                 415

AGC AGA TTA ACT TTT AAA GCG AGC CAG TTG ACC AAG CTG ACC TCC TTG      1473
Ser Arg Leu Thr Phe Lys Ala Ser Gln Leu Thr Lys Leu Thr Ser Leu
            420                 425                 430

GGC AAA TTG GGG GTC AAC GCG ACG ATC GTG ACT AAA TTC AAT AGA GGC      1521
Gly Lys Leu Gly Val Asn Ala Thr Ile Val Thr Lys Phe Asn Arg Gly
435                 440                 445                 450

GCC GAC TGG AAG TTC AAC GTA GTC CTG TAC AAT ACG CCT AAG CTT AGC      1569
Ala Asp Trp Lys Phe Asn Val Val Leu Tyr Asn Thr Pro Lys Leu Ser
            455                 460                 465

AGT ACG ACG GGG ACT ACT TCT TCC TTT GCG ATT CCA ACG GCT TTC AAC      1617
Ser Thr Thr Gly Thr Thr Ser Ser Phe Ala Ile Pro Thr Ala Phe Asn
            470                 475                 480

GGG GAT CAG CTT GCT ACG ATG GAA GCG GTC TAT GTA AAC GGC GGC AAT      1665
Gly Asp Gln Leu Ala Thr Met Glu Ala Val Tyr Val Asn Gly Gly Asn
            485                 490                 495

GCC GGT CCG CAT AAC TGG ACT TCC TTT AAG GAA TTC GAA ACG ACG TTC      1713
Ala Gly Pro His Asn Trp Thr Ser Phe Lys Glu Phe Glu Thr Thr Phe
500                 505                 510

AGC CCC GCT TAT AGC GAG GGG AAA ATC AAA CTG CAG CAG GCG TTC TTT      1761
Ser Pro Ala Tyr Ser Glu Gly Lys Ile Lys Leu Gln Gln Ala Phe Phe
515                 520                 525                 530

AAT GAA GTG AAT GAT ACC ACA GTC ACG CTC AAG TTC CAA TTC TGG AGC      1809
Asn Glu Val Asn Asp Thr Thr Val Thr Leu Lys Phe Gln Phe Trp Ser
            535                 540                 545

GGG GAG ATC GTC AAC TAC ACG ATT AAA AAG AGC GGT TCG ACG GTG ACG      1857
Gly Glu Ile Val Asn Tyr Thr Ile Lys Lys Ser Gly Ser Thr Val Thr
            550                 555                 560

GGT ACG GCT TCA TAAGCGAGTT TGGCAAAAAA GGACCGATAT ACTGCCTAAT          1909
Gly Thr Ala Ser
            565

TTGGTATTGC CTTAGTTGAA AGCAATTGCT CCGAATAAAC AGAATGAAGC CCCGGCCAGC    1969

TGGCCGGGAC TTATGCGTTT AGGAAGTATA AACGAATCAT CAGCAATTTA TTTAGCTCGT    2029

CTCAGTTCAG CAATATCGGC TTCATGTGAA ACGGAGCGGA TGAACAATCT TTCGAGCAAT    2089

TTCTCATGCT CCTGCTGGGT TTGGAGAACG GTTTGCTGAT TAGTTTTAAG TACAGATATA    2149

TCCTCACGGA CTTGATTGAT TCATGTGGTC CGTTAGTTCT TCTACCTTTG TATTTGTGGC    2209

AGCAACGATA TGAATTAATT GTTGAATGTG CCCGCCATGA CTGTTTAGCT GCTCATTGTG    2269

GCTTTGTAAC TGTTCTCGGA TTTCTTTGAA TTCTTGGTCG TGCTCATTAA GCTT          2323

(2) INFORMATION FOR SEQ ID NO:4:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO:4:
```

```
Met Lys Lys Arg Arg Ser Ser Lys Val Ile Leu Ser Leu Ala Ile Val
 1               5                  10                  15

Val Ala Leu Leu Ala Ala Val Glu Pro Asn Ala Ala Leu Ala Ala Ala
            20                  25                  30

Pro Pro Ser Ala Met Gln Ser Tyr Val Glu Ala Met Gln Pro Gly Trp
            35                  40                  45

Asn Leu Gly Asn Ser Leu Asp Ala Val Gly Ala Asp Glu Thr Leu Ala
 50                  55                  60

Arg Gly Asn Pro Arg Ile Thr Lys Glu Leu Ile Gln Asn Ile Ala Ala
 65                  70                  75                  80

Gln Gly Tyr Lys Ser Ile Arg Ile Pro Val Thr Trp Asp Ser His Ile
                85                  90                  95

Gly Ala Ala Pro Asn Tyr Gln Ile Glu Ala Ala Tyr Leu Asn Arg Val
            100                 105                 110

Gln Glu Val Val Gln Trp Ala Leu Asp Ala Asn Leu Tyr Val Met Ile
            115                 120                 125

Asn Val His His Asp Ser Trp Leu Trp Ile Ser Lys Met Glu Ser Gln
 130                 135                 140

His Asp Gln Val Leu Ala Arg Tyr Asn Ala Ile Trp Thr Gln Ile Ala
 145                 150                 155                 160

Asn Lys Phe Lys Asn Ser Pro Ser Lys Leu Met Phe Glu Ser Val Asn
                165                 170                 175

Glu Pro Arg Phe Thr Asp Gly Gly Thr Thr Asp Glu Ala Lys Gln Gln
            180                 185                 190

Lys Met Leu Asp Glu Leu Asn Val Ser Phe Phe Asn Ile Val Arg Asn
            195                 200                 205

Ser Gly Gly Gln Asn Ala Thr Arg Pro Leu Val Leu Ser Thr Leu Glu
 210                 215                 220

Ala Ser Pro Thr Gln Glu Arg Met Thr Ala Leu Tyr Asn Thr Met Thr
 225                 230                 235                 240

Lys Leu Asn Asp Lys Asn Leu Ile Ala Thr Val His Phe Tyr Gly Phe
                245                 250                 255

Trp Pro Phe Ser Val Asn Ile Ala Gly Tyr Thr Lys Phe Asp Ala Glu
            260                 265                 270

Thr Gln Asn Asp Ile Ile Thr Thr Phe Asp Asn Val Tyr Asn Thr Phe
            275                 280                 285

Val Ala Lys Gly Ile Pro Val Val Gly Glu Tyr Gly Leu Leu Gly
 290                 295                 300

Phe Asp Lys Asn Thr Gly Val Ile Glu Gln Gly Glu Lys Leu Lys Phe
 305                 310                 315                 320

Phe Glu Phe Phe Ala Gln Tyr Val Lys Gln Lys Ser Ile Ser Thr Met
                325                 330                 335

Leu Trp Asp Asn Gly Gln His Phe Asn Arg Thr Ser Phe Lys Trp Ser
            340                 345                 350

Asp Pro Asp Leu Phe Asn Met Ile Lys Ala Ser Trp Thr Gly Arg Ser
            355                 360                 365

Ser Thr Ala Ser Ser Asp Leu Ile His Val Lys Gln Gly Thr Ala Val
 370                 375                 380

Lys Asp Thr Ser Val Gln Leu Asn Leu Asn Gly Asn Thr Leu Thr Ser
 385                 390                 395                 400

Leu Ser Val Asn Gly Thr Thr Leu Lys Ser Gly Thr Asp Tyr Thr Leu
                405                 410                 415

Asn Ser Ser Arg Leu Thr Phe Lys Ala Ser Gln Leu Thr Lys Leu Thr
            420                 425                 430
```

```
Ser Leu Gly Lys Leu Gly Val Asn Ala Thr Ile Val Thr Lys Phe Asn
        435                 440                 445

Arg Gly Ala Asp Trp Lys Phe Asn Val Val Leu Tyr Asn Thr Pro Lys
        450                 455                 460

Leu Ser Ser Thr Thr Gly Thr Thr Ser Ser Phe Ala Ile Pro Thr Ala
465                 470                 475                 480

Phe Asn Gly Asp Gln Leu Ala Thr Met Glu Ala Val Tyr Val Asn Gly
                485                 490                 495

Gly Asn Ala Gly Pro His Asn Trp Thr Ser Phe Lys Glu Phe Glu Thr
                500                 505                 510

Thr Phe Ser Pro Ala Tyr Ser Glu Gly Lys Ile Lys Leu Gln Gln Ala
        515                 520                 525

Phe Phe Asn Glu Val Asn Asp Thr Thr Val Thr Leu Lys Phe Gln Phe
        530                 535                 540

Trp Ser Gly Glu Ile Val Asn Tyr Thr Ile Lys Lys Ser Gly Ser Thr
545                 550                 555                 560

Val Thr Gly Thr Ala Ser
                565
```

(2) INFORMATION FOR SEQ ID NO:5:

(i) SEQUENCE CHARACTERISTICS:
        (A) LENGTH: 1775 base pairs
        (B) TYPE: nucleic acid
        (C) STRANDEDNESS: double
        (D) TOPOLOGY: linear (ii) MOLECULE TYPE: DNA (genomic)

(v) FRAGMENT TYPE: N-terminal (vi) ORIGINAL SOURCE:
        (A) ORGANISM: Bacillus lautus
        (B) STRAIN: NCIMB 40250

(ix) FEATURE:
        (A) NAME/KEY: CDS
        (B) LOCATION: 30..(1625.1775)
        (C) IDENTIFICATION METHOD: experimental
        (D) OTHER INFORMATION: /partial
           /evidence= EXPERIMENTAL
           /transl_except= (pos: 1446 .. 1458, aa:
           OTR)

(xi) SEQUENCE DESCRIPTION: SEQ ID NO:5:

```
TTGAAGCGCT GAATTCAGGA GGTTAAATAA TGCGTATTCA TGCAATTCGG CAATCTTGCC      60

GTTTGGTATT GACGATGGTT TTGATGCTTG GCTTATTGCT GCCTGTGGGC GCCCCCAAAG     120

GCTATGCCGC TCCGGCTGTT CCTTTTGGCC AATTAAAAGT TCAGGGCAAT CAATTGGTAG     180

GACAGTCCGG GCAAGCTGTT CAACTGGTTG GCATGAGCTC ACATGGATTG CAGTGGTATG     240

GCAATTTCGT CAACAAATCG TCGTTGCAGT GGATGAGAGA TAACTGGGGC ATCAACGTCT     300

TCCGTGCCGC TATGTATACT TCCGAAGATG GTTACATTAC GGATCCTTCC GTCAAGAACA     360

AGGTGAAGGA GGCGGTTCAG GCATCCATCG ATCTGGCCTT GTACGTTATT ATTGACTGGC     420

ATATCTTGTC TGATGGGAAT CCGAATACGT ACAAAGCGCA ATCGAAAGCG TTCTTCCAAG     480

AGATGGCCAC ATTGTACGGC AACACGCCGA ATGTAATCTA TGAAATCGCG ACGAGCCCAA     540

CGGAATGTGT CCTGGGCAGA TGTCAGTCGT CGGAAGAAGT GATCACGGCC ATTCGTTCGA     600

TTGACCCCGA CGGAGTGGTT ATCGTTGGCA GTCCAACCTG GAGCCAGGAT ATTCATCTGG     660

CGGCCGATAA CCCGGTATCA CATAGCAATG TCATGTATGC GCTTCATTTC TATTCAGGCA     720
```

-continued

```
CGCATGGACA GTTTTTGAGA GACCGAATTA CCTATGCGAT GAACAAAGGA GCAGCGATCT        780

TCGTTACCGA GTGGGGCACC AGTGATGCAT CCGGGAACGG CGGGCCGTAT TTGCCTCAGT        840

CCAAAGAGTG GATCGATTTC TTGAATGCTC GCAAGATCAG CTGGGTGAAC TGGTCGCTCG        900

CTGATAAAGT AGAAACGTCT GCTGCTCTTA TGCCAGGTGC ATCGCCTACC GGCGCTGGAC        960

CGATGCCCAA TTGTCGAATG GGCAAATCGG GTTCGCGATC AAATCCGGCA AGCAACTGGA       1020

GGCGGCAGGG CAATCCAACT GCACCGGCTG CCCCTACTAA CCTCTCGGCA AACGGCGGCA       1080

ACGCCCAGGT ATCATTAACC TGGAACGCAG TTAGCGGGGC GACGAGCTAT ACCGTAAAGC       1140

GAGCAACGAC GAGCGGCGGT CCGTACACGA ATGTGGACCG GGGTGTCACG GCGACGAGCT       1200

ACACGAACAC CGGGCTGACG AATGGCACGA CGTATTATTA TGTCGTGAGG GCATCCAATA       1260

GCGCGGGCAG CAGCGCGAAC TCCGCGCAAG CGAGCGCAAC GCCGGCTAGC GGCGGCGCCA       1320

GTACGGGGAA CCTTGTTGTC CAATACAAAG TTGGCGACAC TAGCGCCACG GATAACCAAA       1380

TGAAGCCTTC CTTTAACATC AAGAACAACG GTACAACCCC TGTTAACCTG AGCGGCCTCA       1440

AGCTTNNNNN NNNNNNNNAA AAAGACGGAC CTGCGGATAT GAGCTGCTCG ATCGACTGGG       1500

CGCAAATCGG CCGAACGAAT GTTCTGCTGG CATTCGCTAA CTTTACCGGG AGTAATACGG       1560

ATACTTACTG TTGTGAGCTA AGCTTTAGCT GCACTGCAGG TTCGTATCCC GGCTATGCGT       1620

GGACNNNNNN NNNNNNNNNN NNNNNNNNNN NNNNNNNNNN NNNNNNNNNN NNNNNNNNNN       1680

NNNNNNNNNN NNNNNNNNNN NNNNNNNNNN NNNNNNNNNN NNNNNNNNNN NNNNNNNNNN       1740

NNNNNNNNNN NNNNNNNNNN NNNNNNNNNN NNNNN                                  1775
```

(2) INFORMATION FOR SEQ ID NO:6:

(i) SEQUENCE CHARACTERISTICS:
        (A) LENGTH: 1624 base pairs
        (B) TYPE: nucleic acid
        (C) STRANDEDNESS: double
        (D) TOPOLOGY: linear (ii) MOLECULE TYPE: protein (v) FRAGMENT TYPE: N-terminal (vi) ORIGINAL SOURCE:
        (A) ORGANISM: Bacillus lautus
        (B) STRAIN: NCIMB 40250

(ix) FEATURE:
        (A) NAME/KEY: CDS
        (B) LOCATION: 30..1607
        (D) OTHER INFORMATION:

(xi) SEQUENCE DESCRIPTION: SEQ ID NO:6:

```
TTGAAGCGCT GAATTCAGGA GGTTAAATA ATG CGT ATT CAT GCA ATT CGG CAA         53
                                Met Arg Ile His Ala Ile Arg Gln
                                 1               5

TCT TGC CGT TTG GTA TTG ACG ATG GTT TTG ATG CTT GGC TTA TTG CTG        101
Ser Cys Arg Leu Val Leu Thr Met Val Leu Met Leu Gly Leu Leu Leu
        10                  15                  20

CCT GTG GGC GCC CCC AAA GGC TAT GCC GCT CCG GCT GTT CCT TTT GGC        149
Pro Val Gly Ala Pro Lys Gly Tyr Ala Ala Pro Ala Val Pro Phe Gly
 25                  30                  35                  40

CAA TTA AAA GTT CAG GGC AAT CAA TTG GTA GGA CAG TCC GGG CAA GCT        197
Gln Leu Lys Val Gln Gly Asn Gln Leu Val Gly Gln Ser Gly Gln Ala
                 45                  50                  55

GTT CAA CTG GTT GGC ATG AGC TCA CAT GGA TTG CAG TGG TAT GGC AAT        245
Val Gln Leu Val Gly Met Ser Ser His Gly Leu Gln Trp Tyr Gly Asn
         60                  65                  70
```

| | | |
|---|---|---|
| TTC GTC AAC AAA TCG TCG TTG CAG TGG ATG AGA GAT AAC TGG GGC ATC<br>Phe Val Asn Lys Ser Ser Leu Gln Trp Met Arg Asp Asn Trp Gly Ile<br>            75                  80                  85 | | 293 |
| AAC GTC TTC CGT GCC GCT ATG TAT ACT TCC GAA GAT GGT TAC ATT ACG<br>Asn Val Phe Arg Ala Ala Met Tyr Thr Ser Glu Asp Gly Tyr Ile Thr<br>        90                  95                 100 | | 341 |
| GAT CCT TCC GTC AAG AAC AAG GTG AAG GAG GCG GTT CAG GCA TCC ATC<br>Asp Pro Ser Val Lys Asn Lys Val Lys Glu Ala Val Gln Ala Ser Ile<br>105                 110                 115                 120 | | 389 |
| GAT CTG GCC TTG TAC GTT ATT ATT GAC TGG CAT ATC TTG TCT GAT GGG<br>Asp Leu Ala Leu Tyr Val Ile Ile Asp Trp His Ile Leu Ser Asp Gly<br>                125                 130                 135 | | 437 |
| AAT CCG AAT ACG TAC AAA GCG CAA TCG AAA GCG TTC TTC CAA GAG ATG<br>Asn Pro Asn Thr Tyr Lys Ala Gln Ser Lys Ala Phe Phe Gln Glu Met<br>            140                 145                 150 | | 485 |
| GCC ACA TTG TAC GGC AAC ACG CCG AAT GTA ATC TAT GAA ATC GCG ACG<br>Ala Thr Leu Tyr Gly Asn Thr Pro Asn Val Ile Tyr Glu Ile Ala Thr<br>        155                 160                 165 | | 533 |
| AGC CCA ACG GAA TGT GTC CTG GGC AGA TGT CAG TCG TCG GAA GAA GTG<br>Ser Pro Thr Glu Cys Val Leu Gly Arg Cys Gln Ser Ser Glu Glu Val<br>170                 175                 180 | | 581 |
| ATC ACG GCC ATT CGT TCG ATT GAC CCC GAC GGA GTG GTT ATC GTT GGC<br>Ile Thr Ala Ile Arg Ser Ile Asp Pro Asp Gly Val Val Ile Val Gly<br>185                 190                 195                 200 | | 629 |
| AGT CCA ACC TGG AGC CAG GAT ATT CAT CTG GCG GCC GAT AAC CCG GTA<br>Ser Pro Thr Trp Ser Gln Asp Ile His Leu Ala Ala Asp Asn Pro Val<br>                205                 210                 215 | | 677 |
| TCA CAT AGC AAT GTC ATG TAT GCG CTT CAT TTC TAT TCA GGC ACG CAT<br>Ser His Ser Asn Val Met Tyr Ala Leu His Phe Tyr Ser Gly Thr His<br>            220                 225                 230 | | 725 |
| GGA CAG TTT TTG AGA GAC CGA ATT ACC TAT GCG ATG AAC AAA GGA GCA<br>Gly Gln Phe Leu Arg Asp Arg Ile Thr Tyr Ala Met Asn Lys Gly Ala<br>        235                 240                 245 | | 773 |
| GCG ATC TTC GTT ACC GAG TGG GGC ACC AGT GAT GCA TCC GGG AAC GGC<br>Ala Ile Phe Val Thr Glu Trp Gly Thr Ser Asp Ala Ser Gly Asn Gly<br>250                 255                 260 | | 821 |
| GGG CCG TAT TTG CCT CAG TCC AAA GAG TGG ATC GAT TTC TTG AAT GCT<br>Gly Pro Tyr Leu Pro Gln Ser Lys Glu Trp Ile Asp Phe Leu Asn Ala<br>265                 270                 275                 280 | | 869 |
| CGC AAG ATC AGC TGG GTG AAC TGG TCG CTC GCT GAT AAA GTA GAA ACG<br>Arg Lys Ile Ser Trp Val Asn Trp Ser Leu Ala Asp Lys Val Glu Thr<br>                285                 290                 295 | | 917 |
| TCT GCT GCT CTT ATG CCA GGT GCA TCG CCT ACC GGC GCT GGA CCG ATG<br>Ser Ala Ala Leu Met Pro Gly Ala Ser Pro Thr Gly Ala Gly Pro Met<br>            300                 305                 310 | | 965 |
| CCC AAT TGT CGA ATG GGC AAA TCG GGT TCG CGA TCA AAT CCG GCA AGC<br>Pro Asn Cys Arg Met Gly Lys Ser Gly Ser Arg Ser Asn Pro Ala Ser<br>        315                 320                 325 | | 1013 |
| AAC TGG AGG CGG CAG GGC AAT CCA ACT GCA CCG GCT GCC CCT ACT AAC<br>Asn Trp Arg Arg Gln Gly Asn Pro Thr Ala Pro Ala Ala Pro Thr Asn<br>330                 335                 340 | | 1061 |
| CTC TCG GCA AAC GGC GGC AAC GCC CAG GTA TCA TTA ACC TGG AAC GCA<br>Leu Ser Ala Asn Gly Gly Asn Ala Gln Val Ser Leu Thr Trp Asn Ala<br>345                 350                 355                 360 | | 1109 |
| GTT AGC GGG GCG ACG AGC TAT ACC GTA AAG CGA GCA ACG ACG AGC GGC<br>Val Ser Gly Ala Thr Ser Tyr Thr Val Lys Arg Ala Thr Thr Ser Gly<br>                365                 370                 375 | | 1157 |
| GGT CCG TAC ACG AAT GTG GAC CGG GGT GTC ACG GCG ACG AGC TAC ACG<br>Gly Pro Tyr Thr Asn Val Asp Arg Gly Val Thr Ala Thr Ser Tyr Thr<br>            380                 385                 390 | | 1205 |

```
AAC ACC GGG CTG ACG AAT GGC ACG ACG TAT TAT TAT GTC GTG AGG GCA        1253
Asn Thr Gly Leu Thr Asn Gly Thr Thr Tyr Tyr Tyr Val Val Arg Ala
            395                 400                 405

TCC AAT AGC GCG GGC AGC AGC GCG AAC TCC GCG CAA GCG AGC GCA ACG        1301
Ser Asn Ser Ala Gly Ser Ser Ala Asn Ser Ala Gln Ala Ser Ala Thr
        410                 415                 420

CCG GCT AGC GGC GGC GCC AGT ACG GGG AAC CTT GTT GTC CAA TAC AAA        1349
Pro Ala Ser Gly Gly Ala Ser Thr Gly Asn Leu Val Val Gln Tyr Lys
425                 430                 435                 440

GTT GGC GAC ACT AGC GCC ACG GAT AAC CAA ATG AAG CCT TCC TTT AAC        1397
Val Gly Asp Thr Ser Ala Thr Asp Asn Gln Met Lys Pro Ser Phe Asn
            445                 450                 455

ATC AAG AAC AAC GGT ACA ACC CCT GTT AAC CTG AGC GGC CTC AAG CTT        1445
Ile Lys Asn Asn Gly Thr Thr Pro Val Asn Leu Ser Gly Leu Lys Leu
        460                 465                 470

NNN NNN NNN NNN NAA AAA GAC GGA CCT GCG GAT ATG AGC TGC TCG ATC        1493
Xaa Xaa Xaa Xaa Xaa Lys Asp Gly Pro Ala Asp Met Ser Cys Ser Ile
            475                 480                 485

GAC TGG GCG CAA ATC GGC CGA ACG AAT GTT CTG CTG GCA TTC GCT AAC        1541
Asp Trp Ala Gln Ile Gly Arg Thr Asn Val Leu Leu Ala Phe Ala Asn
490                 495                 500

TTT ACC GGG AGT AAT ACG GAT ACT TAC TGT TGT GAG CTA AGC TTT AGC        1589
Phe Thr Gly Ser Asn Thr Asp Thr Tyr Cys Cys Glu Leu Ser Phe Ser
505                 510                 515                 520

TGC ACT GCA GGT TCG TAT CCC GGC TAT GCG TGG AC                         1624
Cys Thr Ala Gly Ser Tyr Pro Gly Tyr Ala Trp
            525
```

(2) INFORMATION FOR SEQ ID NO:7:

(i) SEQUENCE CHARACTERISTICS:
        (A) LENGTH: 531 amino acids
        (B) TYPE: amino acid
        (D) TOPOLOGY: linear (ii) MOLECULE TYPE: protein (xi) SEQUENCE DESCRIPTION: SEQ ID NO:7:

```
Met Arg Ile His Ala Ile Arg Gln Ser Cys Arg Leu Val Leu Thr Met
 1               5                  10                  15

Val Leu Met Leu Gly Leu Leu Pro Val Gly Ala Pro Lys Gly Tyr
             20                  25                  30

Ala Ala Pro Ala Val Pro Phe Gly Gln Leu Lys Val Gln Gly Asn Gln
             35                  40                  45

Leu Val Gly Gln Ser Gly Gln Ala Val Gln Leu Val Gly Met Ser Ser
 50                  55                  60

His Gly Leu Gln Trp Tyr Gly Asn Phe Val Asn Lys Ser Ser Leu Gln
 65                  70                  75                  80

Trp Met Arg Asp Asn Trp Gly Ile Asn Val Phe Arg Ala Ala Met Tyr
             85                  90                  95

Thr Ser Glu Asp Gly Tyr Ile Thr Asp Pro Ser Val Lys Asn Lys Val
             100                 105                 110

Lys Glu Ala Val Gln Ala Ser Ile Asp Leu Ala Leu Tyr Val Ile Ile
         115                 120                 125

Asp Trp His Ile Leu Ser Asp Gly Asn Pro Asn Thr Tyr Lys Ala Gln
 130                 135                 140

Ser Lys Ala Phe Phe Gln Glu Met Ala Thr Leu Tyr Gly Asn Thr Pro
 145                 150                 155                 160

Asn Val Ile Tyr Glu Ile Ala Thr Ser Pro Thr Glu Cys Val Leu Gly
             165                 170                 175
```

```
Arg Cys Gln Ser Ser Glu Glu Val Ile Thr Ala Ile Arg Ser Ile Asp
            180                 185                 190

Pro Asp Gly Val Val Ile Val Gly Ser Pro Thr Trp Ser Gln Asp Ile
            195                 200                 205

His Leu Ala Ala Asp Asn Pro Val Ser His Ser Asn Val Met Tyr Ala
            210                 215                 220

Leu His Phe Tyr Ser Gly Thr His Gly Gln Phe Leu Arg Asp Arg Ile
225                 230                 235                 240

Thr Tyr Ala Met Asn Lys Gly Ala Ala Ile Phe Val Thr Glu Trp Gly
            245                 250                 255

Thr Ser Asp Ala Ser Gly Asn Gly Gly Pro Tyr Leu Pro Gln Ser Lys
            260                 265                 270

Glu Trp Ile Asp Phe Leu Asn Ala Arg Lys Ile Ser Trp Val Asn Trp
            275                 280                 285

Ser Leu Ala Asp Lys Val Glu Thr Ser Ala Ala Leu Met Pro Gly Ala
            290                 295                 300

Ser Pro Thr Gly Ala Gly Pro Met Pro Asn Cys Arg Met Gly Lys Ser
305                 310                 315                 320

Gly Ser Arg Ser Asn Pro Ala Ser Asn Trp Arg Arg Gln Gly Asn Pro
                325                 330                 335

Thr Ala Pro Ala Ala Pro Thr Asn Leu Ser Ala Asn Gly Gly Asn Ala
            340                 345                 350

Gln Val Ser Leu Thr Trp Asn Ala Val Ser Gly Ala Thr Ser Tyr Thr
            355                 360                 365

Val Lys Arg Ala Thr Thr Ser Gly Gly Pro Tyr Thr Asn Val Asp Arg
370                 375                 380

Gly Val Thr Ala Thr Ser Tyr Thr Asn Thr Gly Leu Thr Asn Gly Thr
385                 390                 395                 400

Thr Tyr Tyr Tyr Val Val Arg Ala Ser Asn Ser Ala Gly Ser Ser Ala
                405                 410                 415

Asn Ser Ala Gln Ala Ser Ala Thr Pro Ala Ser Gly Gly Ala Ser Thr
            420                 425                 430

Gly Asn Leu Val Val Gln Tyr Lys Val Gly Asp Thr Ser Ala Thr Asp
            435                 440                 445

Asn Gln Met Lys Pro Ser Phe Asn Ile Lys Asn Asn Gly Thr Thr Pro
450                 455                 460

Val Asn Leu Ser Gly Leu Lys Leu Xaa Xaa Xaa Xaa Lys Asp Gly
465                 470                 475                 480

Pro Ala Asp Met Ser Cys Ser Ile Asp Trp Ala Gln Ile Gly Arg Thr
            485                 490                 495

Asn Val Leu Leu Ala Phe Ala Asn Phe Thr Gly Ser Asn Thr Asp Thr
            500                 505                 510

Tyr Cys Cys Glu Leu Ser Phe Ser Cys Thr Ala Gly Ser Tyr Pro Gly
            515                 520                 525

Tyr Ala Trp
            530
```

ENZYME EXHIBITING CELLULASE ACTIVITY

CROSS-REFERENCE TO RELATED APPLICATIONS

This application is a U.S. national stage application under 35 U.S.C. §371 of PCT/DK91/00013 filed Jan. 18, 1991, the contents of which are incorporated herein by reference.

FIELD OF THE INVENTION

The present invention relates to an enzyme exhibiting cellulase activity, a DNA construct encoding the enzyme, a cellulolytic agent comprising the enzyme and a detergent composition containing the enzyme.

BACKGROUND OF THE INVENTION

Biomass which largely consists of cellulose, hemicellulose and lignin has attracted increasing attention as an important renewable source of energy (including nutritional energy). The amount of carbon fixed by photosynthesis has been estimated to be $100 \times 10^9$ tons per year worldwide, and half of that is contained in cellulose. If this material, or at least a significant part of it, could be converted into liquid fuel, gas and feed protein, this would constitute a significant contribution to solving the problem of recycling and conservation of resources. However, it has been found difficult to develop an economically viable process of converting cellulosic material into fermentable sugars.

The currently most promising of the suggested processes involves the use of enzymes which are able to degrade cellulose. These enzymes which are collectively known as cellulases are produced by a number of microorganisms, including fungi (e.g. *Trichoderma reseei, Humicola insolens, Fusarium oxysporum*, etc.) and bacteria (e.g. *Clostridium thermocellum*, Cellulomonas spp., Thermonospora spp., Bacterioides spp., *Microbispora bispora*, etc.). The economics of the production of fermentable sugars from biomass by means of such enzymes is not yet competitive with, for instance, the production of glucose from starch by means of α-amylase due to the ineffeciency of the cellulase enzymes. The most significant problems connected with the use of cellulases is their low specific activity and the high cost of their production. Therefore, there is a need to develop cellulases which are more efficient in degrading cellulosic materials into fermentable sugars.

Apart from their utility for the degradation of biomass, cellulases have also been suggested for use in detergent compositions for the treatment of cotton-containing fabrics which largely consist of cellulose. It is well known that repeated washing of cotton-containing fabrics generally causes a pronounced, unpleasant harshness in the fabric due to the presence of amorphous regions in the cellulose fibres, which regions form protruding parts on the otherwise smooth fibres. Several methods for overcoming this problem have previously been suggested. For example, U.S. Pat. No. 1,368,599 of Unilever Ltd. teaches the use of cellulases for reducing the harshness of cotton-containing fabrics. Also, U.S. Pat. No. 4,435,307 (of Novo Industri A/S) teaches the use of a cellulytic enzyme derived from *Humicola insolens* as well as a fraction thereof as a harshness reducing detergent additive. Other uses of cellulases mentioned in the art include soil removal frown and colour clarification of fabric (cf. for instance EP 220 016).

Although the use of cellulase enzymes for harshness reduction of cotton-containing fabrics was suggested and demonstrated nearly 20 years ago the mechanism of this process has not been elucidated and is still not known in detail. Among other things, this is due to the multiplicity of the enzymes and the enzyme-catalyzed reactions involved. As a matter of fact, cellulases generated in nature e.g. by microbial species are indeed complex mixtures of cellulases. Accordingly, the conversion of naturally occurring materials, like cotton, catalyzed by cellulases is exceedingly difficult to analyze in detail.

Due to these circumstances, the practical exploitation of cellulases for harshness reduction and prevention as well as colour clarification, however desirable, has not become widespread and of great practical utility: it is difficult to optimize production of multiple enzyme systems and thus to implement industrial cost-effective production of cellulase enzymes, and their actual use has been hampered by difficulties arising from the need to employ rather large quantities of the cellulases to achieve the desired reduction and prevention of the harshness of cotton fabrics: for instance, addition of large quantities of the enzymes to detergent compositions is not compatible with the optimal function of other ingredients in the detergent formulation nor is the addition of very large quantities of enzymes to the detergent composition in the interests of, e.g., consumer safety.

The object of the present invention is therefore to provide cellulase enzymes with a high specific activity.

SUMMARY OF THE INVENTION

The present invention relates to an enzyme which exhibits cellulase activity, which enzyme is producible by a strain of Bacillus spp., NCIMB 40250, or by a related Bacillus spp. strain, or a derivative of said cellulase. The strain NCIMB 40250 was deposited on Jan. 18, 1990, in the National Collection of Industrial and Marine Bacteria, 23 St Machar Drive, Aberdeen, Scotland, UK, in accordance with the provisions of the Budapest Treaty on the International Recognition of the Deposit of Microorganisms for the Purpose of Patent Procedure.

In the present context, the expression "enzyme exhibiting cellulase activity" is meant to be understood as an enzyme which is involved in the process of cellulose degradation. There are three different types of cellulases which act synergistically to produce soluble sugars: endoglucanases which show affinity for cellulose and which attack amorphous regions of low crystallinity in the cellulose fiber resulting in the formation of free ends; exoglucanases which initiate degradation from the non-reducing chain ends by removing cellobiose units; and β-glucosidases which hydrolyze cellobiose to glucose.

The expression "related Bacillus spp. strain" is intended to indicate a strain belonging to the same Bacillus species as the strain NCIMB 40250 or a strain of a closely related species. The species to which the strain NCIMB 40250 belongs has been identified as *Bacillus lautus*. The scope of the present invention is also intended at least to include cellulase enzymes producible by other *Bacillus lautus* strains than NCIMB 40250.

The term "derivative" is intended to indicate a protein which is derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence.

Although the enzyme of the invention may be produced by cultivating the Bacillus spp. strain NCIMB 40250 or a related strain and isolating the enzyme from the culture, it will generally be more advantageous to produce the enzyme by recombinant DNA techniques which make it possible to optimize the yield of the enzyme produced. Furthermore, cloned genes encoding the enzymes may be modified in order to provide enzymes with improved properties.

Thus, in another aspect, the present invention relates to a DNA construct which comprises a DNA sequence encoding an enzyme exhibiting cellulase activity, which enzyme is derivable from a strain of Bacillus spp., NCIMB 40250, or a related Bacillus spp. strain, or a derivative of said cellulase. The invention further relates to an expression vector which carries an inserted DNA construct as indicated above, as well as to a cell transformed with the DNA construct or with the vector.

In a still further aspect, the invention relates to a cellulolytic agent capable of degrading amorphous regions of cellulose fibers, the agent comprising an enzyme exhibiting cellulase activity as defined above.

The invention also relates to a detergent composition comprising the cellulolytic agent. The cellulase enzyme of the invention has surprisingly been found to be more stable during washing (for 60 minutes at 40° C.) in the presence of conventional detergents than a commercial cellulose preparation (Celluzyme™, a cellulase preparation isolated from Humicola insolens, available from Novo Nordisk, A/S). The cause of the increased stability may reside in the alkalophilic nature of the enzyme (see example 5 below). It is further speculated that it may also be ascribed to stability towards oxidation or towards the proteases commonly included in detergents. If so, the cellulase enzyme of the invention may also show increased storage stability in liquid detergents containing proteases.

DETAILED DISCLOSURE OF THE INVENTION

The cellulase enzyme of the present invention is preferably one which exhibits endoglucanase activity (referred to in the following as an endoglucanase), in particular one which exhibits an endoglucanase activity of at least about 10, more preferably at least about 20, most preferably at least about 25, such as about 30, CMC-endoase units per mg of total protein under alkaline conditions. The endoglucanase activity is determined as the viscosity decrease of a solution of carboxymethyl cellulose (CMC) after incubation with the enzyme of the present invention under the following conditions:

A substrate solution is prepared, containing 35 g/l CMC (Hercules 7 LFD) in 0.1 M tris buffer at pH 9.0. The enzyme sample to be analyzed is dissolved in the same buffer.

10 ml substrate solution and 0.5 ml enzyme solution are mixed and transferred to a viscosimeter (e.g. Haake VT 181, NV sensor, 181 rpm), thermostated at 40° C.

Viscosity readings are taken as soon as possible after mixing and again 30 minutes later. The amount of enzyme that reduces the viscosity by one half under these conditions is defined as 1 CMC-endoase unit.

It should be noted that the endoglucanase of the invention is one which is active (in terms of CMC-endoase activity) under alkaline conditions. More specifically, the endoglucanase is one which has a pH optimum at a pH of about 7.5–10.5. Contrary to several known cellulases which are active at an acid pH and relatively inactive at alkaline pH values, this characteristic makes the endoglucanase of the invention particularly useful for washing purposes, in particular as an ingredient of a detergent composition, as washing of clothes is typically conducted under alkaline conditions due to the alkalinity of most washing detergents. Alkalophilic cellulases are known, e.g. from EP 271 004, but they are not indicated to have a high affinity for cellulose, which is the case with the cellulase enzyme of the present invention which also exhibits a higher specific activity.

The enzyme of the present invention is preferably one which is active at the temperatures at which clothes are typically washed, which is usually a temperature of up to about 60° C. Thus, the native enzyme isolated from strain NCIMB 40250 is active at temperatures between about 45 and 65° C. This, however, does not preclude the possibility that the enzyme may, under certain conditions, be active at temperatures above 65° C.

One enzyme according to the invention is an endoglucanase with an apparent molecular weight of 75 kD or a cleavage product thereof exhibiting endoglucanase activity. The term "cleavage product" is intended to indicate a shorter form of the enzyme resulting from, for instance, chemical or enzymatic cleavage (e.g. by means of a suitable protease) after recovery of the enzyme or from posttranslational processing by the organism producing the enzyme, e.g. N- and/or C-terminal processing, which may give rise to a mature form of the enzyme. A specific example of a cleavage product of the ~75 kD enzyme which is of interest for the present purpose is a product of approximately 58 kD produced on cultivating a host organism transformed with DNA encoding the ~75 kD enzyme. The ~75 kD enzyme (and its ~58 kD cleavage product) are referred to in the following examples as Endo1.

The enzyme of the invention may be an endoglucanase encoded by the DNA sequence shown in the appended Sequence Listing ID#1 (showing the sequence of the ~75 kD enzyme), or a modification thereof encoding a derivative of said endoglucanase.

Endoglucanase derivatives may conveniently be provided by suitably modifying the DNA sequence coding for the native endoglucanase. Examples of suitable modifications of the DNA sequence are nucleotide substitutions which do not give rise to another amino acid sequence of the endoglucanase, but which may correspond to the codon usage of the host organism into which the DNA construct is introduced or nucleotide substitutions which do give rise to a different amino acid sequence and therefore, possibly, a different polypeptide structure without, however, impairing the properties of the endoglucanase. Other examples of possible modifications are insertion of one or more nucleotides into the sequence, addition of one or more nucleotides at either end of the sequence and deletion of one or more nucleotides at either end of or within the sequence. Such modifications of DNA coding for native proteins are well known and widely practiced in the art.

Another enzyme according to the invention is an endoglucanase with an apparent molecular weight of 56 kD or a cleavage product thereof (as defined above) exhibiting endoglucanase activity. In example 2 below, this enzyme is referred to as Endo2.

The enzyme of the invention may be an endoglucanase encoded by the DNA sequence shown in the appended Sequence Listing ID#3 (showing the sequence of the ~56 kD enzyme), or a modification thereof (as defined above) encoding a derivative (as defined above) of said endoglucanase.

A further enzyme according to the invention is an endoglucanase with an apparent molecular weight of 45 kD or a cleavage product thereof (as defined above) exhibiting endoglucanase activity. A specific example of such a cleavage product is a protein of approximately 30 kD produced on cultivating a host organism transformed with DNA encoding the ~45 kD enzyme. In example 3 below, the ~45 kD enzyme is referred to as Endo3A.

The enzyme of the invention may be an endoglucanase encoded by the DNA sequence shown in the appended sequence Listing ID#5 (showing the DNA sequence encoding the ~45 kD product), or a modification thereof (as defined above) encoding a derivative (as defined above) of said endoglucanase.

Other enzymes exhibiting endoglucanase activity produced from endoglucanase clone 3 (cf. example 3 below) are proteins of approximately 60 and 56 kD, referred to as Endo3B and Endo3C, respectively.

A still further enzyme according to the invention is an endoglucanase with an apparent molecular weight of 92 kD or a cleavage product thereof (as defined above) exhibiting endoglucanase activity. In example 4 below, this enzyme is referred to as Endo4. Other enzymes exhibiting endoglucanase activity produced from endoglucanase clone 4 (cf. example 4 below) are proteins of approximately 74 and 71 kD. Either or both of these may be individual enzymes or cleavage products of the ~92 kD enzyme.

It has been found that enzymes of the invention, e.g. Endo1 and Endo3A, are composed of a core region comprising the catalytically active domain and a region comprising a domain whose function is to mediate binding to cellulosic substrates (i.e. the cellulose-binding domain; this corresponds to a similar domain in an endocellulase from *Bacillus subtilis* (Nakamura et al., 1987). For example, the full-length ~75 kD form of Endo1 comprises a core region and a C-terminal cellulose-binding domain which, in some cases, may be cleaved off proteolytically leaving a core region of ~58 kD. The presence of the cellulose-binding domain has been found to be important for obtaining a color clarification effect in prewashed textiles (cf. example 6 below).

Based on this finding, it may be possible to generate novel derivatives of cellulase enzymes which, for instance, combine a core region derived from an endoglucanase of the present invention with a cellulose-binding domain derived from another cellulase enzyme (e.g. one derived from a *Cellulomonas fimi* cellulase). Alternatively, it may be possible to combine a core region derived from another cellulase enzyme with a cellulose-binding domain derived from an endoglucanase of the present invention. In a particular embodiment, the core region may be derived from a cellulase enzyme which does not, in nature, comprise a cellulose-binding domain, and which is C-terminally extended with a cellulose-binding domain derived from an endoglucanase of the present invention. In this way, it may be possible to construct cellulase enzymes with improved binding properties.

The DNA construct of the invention may be one which comprises a DNA sequence encoding any one of the enzymes described above, or derivatives of these enzymes as defined above. The DNA construct may be of genomic or cDNA origin, for instance obtained by preparing a genomic or cDNA library of an appropriate Bacillus spp. strain (e.g. strain NCIMB 40250 or a related strain) and screening for DNA sequences coding for all or part of the appropriate cellulase by hybridization using synthetic oligonucleotide probes in accordance with standard techniques (cf. Maniatis et al., 1982).

The expression vector of the invention carrying the inserted DNA construct encoding the enzyme of the invention may be any vector which is capable of replicating autonomously in a given host organism, typically a plasmid or bacteriophage. In the vector, the DNA sequence encoding the enzyme of the invention should be operably connected to a suitable promoter sequence. The promoter may be any DNA sequence which shows transcriptional activity in the host cell and may be derived from genes encoding proteins either homologous or heterologous to the host organism. The promoter is preferably derived from a gene encoding a protein homologous to the host organism. Examples of suitable promoters are lac of *E. coli,* dagA of *Streptomyces coelicolor* and amyL of *Bacillus licheniformis.*

The expression vector of the invention further comprises a DNA sequence enabling the vector to replicate in the host cell. Examples of such sequences are the origins of replication of plasmids pUC19, pACYC177, pUB110 and pIJ702.

The expression vector may further comprise a DNA sequence coding for a signal peptide in order to provide extracellular expression of the enzyme. The DNA sequence may, for instance, be the signal sequence from the a-amylase gene of *B. licheniformis.*

The vector may also comprise a selectable marker, e.g. a gene whose product confers antibiotic resistance, such as ampicillin, chloramphenicol or tetracycline resistance, or the dal genes from *B. subtilis* or *B. licheniformis.*

The procedures used to ligate the DNA sequences coding for the enzyme of the invention and the promoter, respectively, and to insert them into suitable vectors containing the information necessary for replication in the host cell, are well known to persons skilled in the art (cf., for instance, Maniatis et al., op.cit.).

The host cell of the present invention may be transformed with the DNA construct of the invention encoding the cellulase enzyme described above. In this case, the DNA construct may conveniently be integrated in the host chromosome which may be an advantage as the DNA sequence coding for the cellulase is more likely to be stably maintained in the cell. Integration of the DNA constructs into the host chromosome may be performed according to conventional methods, e.g. by homologous recombination.

Alternatively, the host cell may be transformed with an expression vector as described above.

The host cell used in the process of the invention may be any suitable bacterium which, on cultivation, produces large amounts of the enzyme of the invention. Examples of suitable bacteria may be grampositive bacteria such as bacteria belonging to the genus Bacillus, e.g. *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans* or *Bacillus lautus,* or gramnegative bacteria such as *Escherichia coli.* The transformation of the bacteria may for instance be effected by protoplast transformation or by using competent cells in a manner known per se.

In a yet further aspect, the present invention relates to a method of producing a cellulase enzyme of the invention, which method comprises cultivating a host cell as described above under conditions conducive to the production of the cellulase or derivative thereof and recovering the cellulase or derivative thereof from the cells and/or culture medium.

The medium used to cultivate the cells may be any conventional medium suitable for growing bacteria. The cellulase may be recovered from the medium by conventional procedures including separating the cells from the medium by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

In a particular embodiment of the method of the invention, the cellulase is recovered in mature form, either as a result of posttranslational processing of a proenzyme as explained above or as a result of appropriate modifications of the DNA sequence encoding the enzyme in the form of deletions of DNA corresponding to truncations in the N- and/or C-terminal sequences of the enzyme.

There is reason to believe that different cellulases may exert a synergistic effect with respect to the degradation of cellulose. The cellulolytic agent of the invention may therefore advantageously comprise a combination of two or more cellulase enzymes of the invention or a combination of one or more cellulase enzymes of the invention with one or more other enzymes exhibiting cellulase activity. Such cellulases may be endocellulases or exocellulases dependent on the intended use of the cellulolytic agent (e.g. the degree of cellulose degradation aimed at). The other cellulases may be selected from those which may be isolated from species of Humicola such as *Humicola insolens* (e.g. strain DSM 1800), Fusarium such as *Fusarium oxysporum* (e.g. strain DSM 2672), Myceliopthora such as *Myceliopthora thermophile*, Erwinia such as *Erwinia chrysanthermis* (cf. M. H. Boyer et al., *Eur. J. Biochem.* 162, 1987, pp. 311–316), Trichoderma such as *Trichoderma reseei*, Microbispora such as *Microbispora bispora*, Neocallimastix such as *Neocallimastix frontalis*, Piromonas such as *Piromonas communis*, Robillarda spp., Cellulomonas such as *Cellulomonas fimi*, Clostridium such as *Clostridium thermocellum*, Pseudomonas spp., Thermonospora spp., Bacterioides spp. or Ruminococcus spp.

The cellulolytic agent of the invention may suitably be in the form of a non-dusting granulate, stabilized liquid or protected enzyme. Non-dusting granulates may be produced e.g. according to U.S. Pat. Nos. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238, 216.

The cellulolytic agent may suitably exhibit an endoglucanase activity of 500–10,000 CMC-endoase units (as defined above) per gram of the agent. The cellulolytic agent is suitably a detergent additive which may comprise one or more other enzymes, such as a protease, lipase and/or amylase, conventionally included in detergent additives.

The detergent composition of the invention comprising the cellulolytic agent described above additionally comprises one or more surfactants which may be of the anionic, non-ionic, cationic, amphoteric, or zwitterionic type as well as mixtures of these surfactant classes. Typical examples of anionic surfactants are linear alkyl benzene sulfonates (LAS), alpha olefin sulfonates (AOS), alcohol ethoxy sulfates (AES) and alkali metal salts of natural fatty acids.

The detergent composition of the invention may contain other detergent ingredients known in the art as e.g. builders, bleaching agents, bleach activators, anti-corrosion agents, sequestering agents, anti soil-redeposition agents, perfumes, enzyme stabilizers, etc.

The detergent composition of the invention may be formulated in any convenient form, e.g. as a powder or liquid. The enzyme may, if required, be stabilized in a liquid detergent by inclusion of enzyme stabilizers as indicated above. Usually, the pH of a solution of the detergent composition of the invention will be 7–12 and in some instances 7.0–10.5. Other detergent enzymes such as proteases, lipases or amylases may be included in the detergent composition of the invention, either separately or in a combined additive as described above.

The softening, soil removal and color clarification effects obtainable by means of the cellulase enzyme of the invention generally require a concentration of the cellulase in the washing solution corresponding to an endoglucanase activity of 5–200 CMC-endoase units per liter. The detergent composition of the invention is typically employed in concentrations of 0.5–20 g/l in the washing solution. Consequently, the cellulase concentration of the detergent composition of the invention is about 0.3–400 CMC-endoase units per gram. In general, it is most convenient to add the detergent additive in amounts of 0.1–5% w/w or, preferably, in amounts of 0.2–2% of the detergent composition. For special applications, however, for instance when the detergent composition is to be used for color clarification or harshness reduction of fabric which has been damaged by repeated washing, it may be convenient to include a much larger amount of the cellulolytic agent, such as about 20% w/w.

In a still further aspect, the present invention relates to a method of reducing the rate at which cellulose-containing fabrics become harsh or of reducing the harshness of cellulose-containing fabrics, the method comprising treating a cellulose-containing fabric with a cellulolytic agent as described above. The method of the invention may be carried out by treating cellulose-containing fabrics during washing. The cellulolytic agent may either be added as such in the amount required to obtained the desired effect, or it may be added as an ingredient of a detergent composition as described above. However, if desired, treatment of the fabrics may also be carried out during soaking or rinsing or simply by adding the cellulolytic agent to water in which the fabrics are or will be immersed.

The cellulolytic agent of the invention may also be employed to obtain color clarification of cellulose-containing fabrics. After repeated washing, such fabrics often develop a grayish appearance. This effect is particularly evident with colored fabrics, especially dark fabrics, and may probably be ascribed to undyed parts of the cellulose fibers becoming apparent when the cellulose fibers of which the fabric is composed are damaged by mechanical forces. The damaged parts of the fibers are assumed to be more amorphous than intact cellulose fibers and therefore more susceptible to the action of the cellulases of the present invention. The color clarification effect is more pronounced when the cellulolytic agent contains an endoglucanase which comprises a cellulose-binding domain (cf. example 6 below).

Accordingly, the present invention further relates to a method of treating a colored, cellulose-containing fabric in order to provide color clarification, the method comprising treating the cellulose-containing fabric with a cellulolytic agent according to the invention. The method of the invention may be carried out by treating cellulose-containing fabrics in an aqueous medium during washing. The cellulolytic agent may either be added as such in the amount required to obtained the desired effect, or it may be added as an ingredient of a detergent composition as described above.

However, if desired, treatment of the fabrics may also be carried out during soaking or rinsing or simply by adding the cellulolytic agent to water in which the fabrics are or will be immersed. For color clarification purposes, the aqueous medium may suitably exhibit an endoglucanase activity of more than about 250 CMC-endoase units per liter of the aqueous medium.

It may furthermore be possible to employ a cellulolytic agent according to the invention to provide a localized variation in the color of a fabric to impart a "stone-washed" appearance to the fabrics (for the use generally of cellulase enzymes for this purpose, see for instance EP 307 564).

The cellulolytic agent of the invention is also contemplated to be useful in the field of paper pulp processing, e.g. pulp drainage (for the use generally of cellulase enzymes for this purpose, see for instance EP 262 040), as well as for de-inking of paper intended for recycling (for the use generally of cellulase enzymes for this purpose, see for instance JP 59-9299 or JP 63-59494).

BRIEF DESCRIPTION OF THE DRAWINGS

The invention is further illustrated by the following examples which are not in any way intended to limit the scope of the invention, with reference to the appended drawings, wherein FIG. 1 Restriction maps of the Bacillus spp. DNA insert contained on the plasmids in the 4 endoglucanase-positive E. coli clones. The position and direction of transcription of endoglucanase 1 (Endo1, pPL517) and endoglucanase 2 (Endo2, pPL382) is indicated. Restriction enzyme sites are indicated as follows: PstI (P), HindIII (H), SmaI, (S), SalI (Sa), BamHI (Ba), BglII (B), SphI (Sp), EcoRI (E). ▬ indicates pBR322 DNA.

EXAMPLES

Figure 2:
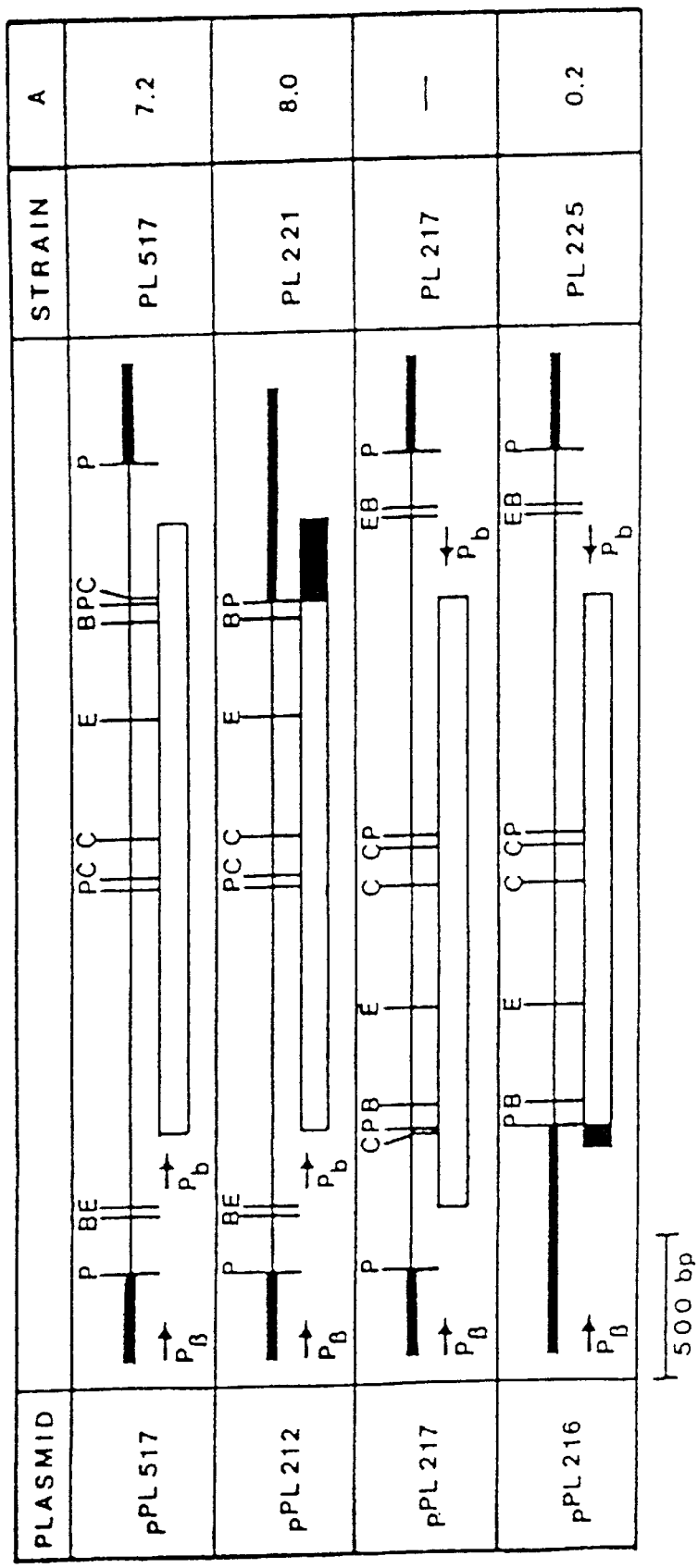
FIG. 2 Restriction maps of different plasmids carrying the Endo1 gene (☐). The β-lactamase promoter of pBR322 is indicated by the arrow (Pb) and the direction of the transcription of the Endo1 gene is indicated by the arrow (Pb). (▬): pBR322, (▬): "tail" of pBR322 encoded amino acids. Restriction enzyme sites are indicated as follows: PstI (P), BalII (B), EcoRI (E), ClaI (C). The endoglucanase activity in extracts of E. coli MC1000 containing the indicated plasmids is shown to the right as (A) cellulase units/ml culture medium.

Materials and Methods a) Bacterial strains and plasmids

The donor strain, Bacillus spp., strain PL236, was isolated from a compost sample from Lyngby, Denmark, on the basis of its high cellulolytic activity. A sample of this strain was deposited on 18 Jan. 1990 in the National Collection of Industrial and Marine Bacteria, 23 St. Machar Drive, Aberdeen, Scotland, with the accession No. NCIMB 40250.

The following E. coli strains and plasmid were used: MC 1000 (araD139), (ara, leu)7697, lacX74, galU, galK, rpsL) (Casabadan et al., 1980); CSR603 (F−, thr-1, leuB6, proA2, prh-1, RecA1, argE3, thi-1, uvrA6, ara-14, lacY1, galK2, xyl-5, mtl-1, rpsL31, tsx-33, −, supE44) (Sancar et al., 1979); PL248 is MC1000 containing the plasmid pNF2690 which contains the replication origin and the kanamycin resistance gene from pACYC177 (Chang and Cohen, 1978) and the cI857 repressor gene from the coliphage lambda; pBR322 (Bolivar, 1977); pUN121 (Nilsson et al., 1983) pUC18 (Yanisch-Perron et al., 1985); pPLc28 (Remaut et al., 1981); pPL170 (Jørgensen, P. L., 1983);

For the experiments with B. subtilis, the following B. subtilis strains and plasmids were used: DN1885 (amyE, amyR, spo+, pro+) (Diderichsen, Novo Industri A/S) is a derivative of B. subtilis 168; PL1801 is a derivative of DN1885 lacking the two main exoproteases (apr−, npr−); pDN2801 has the origin of replication from pUB110 (Keggins et al., 1987), the Cat gene of pC194 (Horinouchi and Weisblum, 1982) and the maltogenic alpha-amylase promoter (Pm) from *B. stearothermophilus* (Diderichsen and Christiansen, 1988) followed by a polylinker; The *B. subtilis/E. coli* shuttle vector pJKK3-1 is described by Kreft et al. (1983); pPL1759 has the origin and kanamycin resistance gene of pUB110 and the promoter, ribosome binding site and signal sequence from the alpha-amylase gene from *B. licheniformis* (Stephens et al., 1984).

b) Media

Phosphoric acid swollen cellulose (ASC) was prepared from chromatography cellulose (MN 300, Machery, Nagel) as described by Walseth (1952) with the exception that the cellulose powder was suspended in acetone before treatment with phosphoric acid. The medium for detection of cellulase activity was prepared as standard m)-medium (Maniatis et al., 1982) containing 0.2% ASC or microcrystalline cellulose. (Avicel, Merck).

Bacillus spp, *B. subtilis* and *E. coli* cells were grown in NY medium (von Meyenburg et al., 1982), LB medium (Maniatis et al., 1982), or BPX medium (100 g/l potato starch, 50 g/l barley flour, 0.1 g/l BAN 5000 SKB, 10 g/l sodium caseinate, 20 g/l soybean meal, 9 g/l $Na_2$ $HPO_4$, $12H_2O$, 0.1 g/l Pluronic).

The media were solidified by the addition of agar (20 g/l).

Tetracycline (20 μg/ml), or kanamycin (10 μg/ml) were added as required.

c) Isolation of DNA

To isolate the chromosomal DNA from Bacillus spp. PL236, cells from 250 ml overnight culture were resuspended in 10 ml (50 mM Tris-HCl, pH 8.0, 100 mM EDTA), and incubated with 25 mg lysozyme for 20 min. at 37° C. To the mixture was added 2 ml of 10% (w/v) SDS, mixed and put on ice for 10 min. To the solution was then added 15 ml of phenol saturated with TE-buffer (10 mM Tris-HCl, pH 8.0, 1 mM EDTA), heated to 65° C., mixed gently and cooled on ice. After centrifugation for 30 min. at 40000 g the aqueous phase was ether extracted, ethanol precipitated and the pellet was resuspended in TE-buffer. The DNA was further purified by banding in a CsCl density gradient (Maniatis et al., 1982).

*E. coli* plasmid DNA was prepared by the SDS lysis method (Maniatis et al., 1982); minipreparations of plasmid DNA for restriction enzyme analysis and transformations were prepared according to Holmes and Quigley (1981). *B. subtilis* plasmid DNA was prepared by the alkaline lysis method. (Maniatis et al., 1982).

d) Cloning of chromosomal DNA from Bacillus spp. PL236 into *E. coli*

Restriction enzymes and T4 DNA ligase were obtained from New England Biolabs and used as described by the manufacturers. After digestion with PstI, EcoRI or HindIII restriction enzyme the DNA was heated to 65° C. for 10 min. and ethanol precipitated. 10 μ of linearized pBR322, pJKK3-1 or pUN121 and 20 g of fragmented B. spp. chromosomal DNA were ligated with 5 units of DNA ligase in a final volume of 100 μl (16 h, 15° C.). The ligated DNA was used to transform competent *E. coli* MC1000 to tetracycline resistance essentially as described by Mandel and Higa (1970). (pBR322: 20 μg/ml, pUN121: 7 μg/ml and pJKK3-1: 10 μg/ml).

e) Detection of cellulase-positive *E. coli* clones

The detection of cellulase activity on plates was performed using a modification of the technique of Teather and Wood (1982). *E. coli* clones were grown overnight on solid NY medium at 37° C. Cells were lysed by overlaying the colonies by topagar containing phosphate buffer (100 mM, pH 7.0), agar (0.7%) CMC (0.2%), SDS (0.25 mg/ml), and chloramphenicol (200 μ/ml) and subsequent incubation overnight at 37° C. Plates were then flooded with an aqueous solution of Congo red (1 mg/ml) for 15 min. and subsequently washed with 1 M NaCl. Cellulase-positive colonies were surrounded by a yellow halo on a red background.

f) Maxicells

Plasmid-encoded proteins were analyzed using the maxicell method of Sancar et al. (1979) with the following modification. After UV irradiation, the surviving cells were killed by incubating the cells with D-cycloserine (150 μg/ml) for 48 h at 37° C.

g) Gel electrophoresis ($^{35}$S)-L.methionine labelled maxicell proteins and other proteins were analyzed by electrophoresis on 15% (0.075 per cent bisacrylamide) SDS-polyacrylamide gels (Laemmli, 1970). Proteins were visualized either by staining with Coomassie Blue G 250 or by autoradiography.

Analysis of DNA was done by electrophoresis on agarose gels with the buffer described by Loening (1967).

h) Detection of cellulase activity in polyacrylamide gels

Detection of cellulase activity in protein bands separated by SDS-polyacrylamide gel electrophoresis was done by a modified zymogram technique described by Beguin (1983). Protein preparations were electrophoresed on a SDS-polyacrylamide gel as described above and the gel was washed 3 times 30 min. in phosphate buffer (100 mM, pH 7.0) layered on to a thin (0.8 mm) agarose gel (agarose, (1.8 per cent), CMC, (0.2 per cent), phosphate buffer, (100 mM, pH 7.0)), and incubated for 4 h at 42° C. Cellulase activity was visualized by staining the agarose gel for 30 min. in an aqueous solution of Congo red (1 mg/ml) followed by washing the gel in 1 M NaCl.

i) Colorimetric cellulase assay

Cellulase activity in cell extracts was analyzed by measuring the increase in reducing groups released by the hydrolysis of CMC (Miller, 1959). An appropriate amount of enzyme was incubated with 1.5 ml of 1 per cent CMC in phosphate buffer (100 mM, pH 7.0). After 30 min. of incubation at 55° C., 1.5 ml of dinitrosalicyclic acid reagent was added and the samples were boiled for 5 min. The absorbance was read at 550 nm against blanks containing equivalent amounts of extract from the *E. coli* recipient strain. One unit of cellulase released 1 nM of glucose equivalents per second by reference to a standard curve.

j) DNA-Sequencing

Single end labelled DNA fragments were isolated and sequenced by the chemical modification method (Maxam and Gilbert, 1980). The cleavage products were separated on 8% or 20% polyacryl-amide gels and thereafter autoradiographed at -70° C. using intensifying screens.

The dideoxyribonucleotide method of Sanger et al., (1977) was used for the sequencing of Endo3A using derivatives of pUC18 (Yanisch-Perron, 1985).

k) Southern analysis

Chromosomal DNA from Bacillus spp. (PL236) was digested with restriction enzymes as required and fractionated on 1% (w/v) agarose gels. DNA was then blotted onto nitrocellulose filters. $32_p$-labelled DNA probes (recombinant plasmids) were prepared by nick translation (Rigby et al., 1977) using $32_{p\text{-}dCTP}$ (Amersham) and hybridization was carried out as described by Southern (1975). Autoradiography was performed at -70° C. using intensifying screens.

l) Transformation of competent *B. subtilis* cells

A modified version of Dubnau and Davidoff-Adelson's (1971) procedure for preparing competent cells of *B. subtilis* is used. 10 ml of LB-medium is inoculated with the strain in the morning. 7 hours later sequential dilutions in KM-1- medium are made and incubated overnight at 37° C. The following morning, the second-most diluted and growing culture is diluted ten times in KM-2-medium. The cells are harvested after 45–60 minutes of incubation by centrifuging for 3 minutes at 7 K. They are resuspended in 1/10 volume of the supernatant and 1/50 volume of 86% glycerol is added. 0.1 ml amounts are frozen on liquid nitrogen and stored at −80° C.

In order to transform these competent cells, the method of Ehrlich (1986) is used, with some modifications. BTF is prepared and preheated to 42° C. 0.01 ml of DNA is placed in a reaction vessel, and the competent cells are thawed at 42° C. BTF is added to the cells at a ratio of 1:1, and 0.1 ml of the mixture is added to the DNA. The cells and DNA incubate with shaking for 20 minutes at 37° C. A further 30 minutes of gene expression with 0.1 ml of NY-medium is needed, if kanamycin resistance is desired. The cells are finally spread on relevant plates. Recipes for stock-solutions are as follows:

| Stock solutions for making B. subtilis competent cells | |
|---|---|
| Salt mix: | 10 mM $CaCl_2$, 1mM $FeCl_3$ and 1mM $MnCl_2$. |
| 10 × MM: | 20 g $(NH_4)_2SO_4$, 60 g $KH_2PO_4$, 140 g $K_2HPO_4 \cdot 3H_2O$ in 1L. |
| KM-stock: | 100 ml 10 × MM, 10 ml 10% Na-citrate, 2 ml 1M $MgSO_4$ in 1L. |
| KM1-stock: | 960 ml KM-stock, 20 ml 20% glucose, 1 ml 20% casamino acids, 20 ml 5% yeast extract, 30 1 1mM $MnCl_2$ in 1L. |
| KM2-stock: | 960 ml KM-stock, 20 ml 20% glucose, 1 ml 20% casamino acids, 20 ml 5% yeast extract, 1 ml salt mix, 1 ml 0.5 M $CaCl_2$, and 0.8 ml 1M $MgCl_2$ in 1L. |
| BCG: | 100 ml 10 × MM, 10 ml Na-citrate, 2 ml 1M MgSO, 1 ml saltmix, 20 ml 20% glucose in 1L. |
| BTF: | 800 ml BCG, 100 ml 10mM EGTA, 100 mM $MgCl_2$ in 1L. (Prepared fresh before use). |

Isolation and Characterization of Cellulolytic Strains

In order to clone genes coding for cellulose-degrading enzymes the following screening program was set up to find suitable cellulolytic donor strains. Various compost samples were used as source of cellulolytic microorganisms.

Serial dilutions of compost samples were plated out on ASC agar medium and cellulolytic activity was detected through the formation of clearing zones around the colonies. Several cellulolytic bacteria were isolated. One of the most active of these isolates which was identified as Bacillus spp. PL236 (NCIMB 40250) was selected as the donor strain for the cloning experiments.

The strain rapidly degraded both acid swollen cellulose and microcrystalline cellulose (Avicel, Merck) on agar medium. At the optimum temperature of growth (42° C.) the clearing zones appeared in 2–3 days.

Adding small amounts of Bacillus spp. PL236 culture to suspensions of microcrystalline cellulose makes the cellulose crystals lump together tightly and sediment.

This suggests that either the Bacillus spp. PL236 cells or the extracellular cellulase enzymes have a strong affinity for the cellulose substrate and tightly bind the cellulose crystals together.

Screening Assay for Recombinant Clones

The first attempts to clone cellulases from Bacillus spp. PL236 were directed towards the endocellulases genes from Bacillus spp. PL236. To facilitate the screening on plates of endocellulase positive clones, an assay using the dye Congo red (Teather and Wood, 1982) was adapted to E. coli.

In order to detect cellulase activity trapped inside the recombinant E. coli cells the cells were lysed by adding SDS to the top agar. This modification of the top agar had no measurable effect on the CMC-degrading enzymes of Bacillus spp. PL236, when the modified assay was used on this organism.

Molecular Cloning of Endocellulases

Several endocellulase genes were cloned from the cellulolytic Bacillus spp. strain (PL236). An endocellulase 1 clone (PL517) was made by ligating PstI partially digested PL236 chromosomal DNA with PstI cleaved pBR322 and subsequently transforming competent E. coli cells.

An endocellulase 2 clone (pPL382) was made by ligating HindIII partially digested PL236 chromosomal DNA with HindIII cleaved pJKK3-1 (an E. coli/B. subtilis shuttle-vector) and subsequently transforming competent E. coli cells.

An endocellulase 3 clone (pPL591) was made by ligating EcoRI partially digested PL236 DNA with EcoRI cleaved pUN121 and subsequently transforming competent E. coli cells.

An endocellulase 4 clone (pPL592) was made by ligating HindIII partially digested PL236 DNA with HindIII cleaved pUN121 and subsequently transforming competent E. coli cells.

Transformants derived from the use of both the pBR322 and the pUN121 plasmid vector were screened by their tetracycline resistance (pBR322: 20 g/ml, pUN121: 7 µg/ml and pJKK3-1: 10 µg/ml).

The transformants were replicated to another set of plates and overlayed by the modified CMC top agar. The plates were incubated overnight and stained with Congo red as described above.

Under the reisolation procedure it was observed that it was possible to detect positive clones without adding the cell lyzing agent SDS to the topagar, although the diameter of the halo was considerably smaller.

Expression and Characterization of the Cloned Cellulases

Plasmids from the cellulase-positive transformants were isolated and analyzed with restriction enzymes. Restriction enzyme maps of representative plasmids from all four cloning experiments are shown in FIG. 1.

To determine the molecular weight of the cloned endoglucanases a zymogram technique (Beguin, 1983) was used. Total protein preparations from representative endoglucanase clones were separated on a SDS-polyacrylamide gel. The proteins in the gel were then renatured by washing out the SDS and replicated onto an agarose gel containing CMC. Renatured proteins diffuse to this activity gel and proteins representing endoglucanase activity hydrolyze the CMC in the gel. The endoglucanase bands were then visualized by staining the activity gel with Congo red as described above.

As appears from FIG. 1, the restriction maps of the cloned DNA (as well as the molecular weight of the endoglucanases encoded by the cloned DNA) are different in the four different clones. This indicates that these four clones represent at least four different endocellulase genes from Bacillus spp. (PL236).

The detailed analysis of the different endocellulases represented by these four clones is described in the following.

EXAMPLE 1
Endocellulase 1 (Endo1)
Physical mapping of endocellulase gene 1

In the cloning experiment described above several cellulase-positive *E. coli* clones were obtained, which contained different fragments of PstI partially cleaved Bacillus spp. PL236 DNA. FIG. 2 shows the restriction maps of some of these clones. The plasmids invariably contained two PstI fragments (1000 and 1350 bp.) indicating that both were necessary for synthesis of a polypeptide with cellulase activity: Nucleotide sequencing has later shown that the 500 bp. PstI fragment present the on pPL217 and pPL517 (FIG. 2) contains the C-terminal part of the complete cellulase gene (data are presented in the following). The structure of this part of the B.spp. chromosome was confirmed by Southern analysis (data are presented in the following).

Activity measurements

Extracts from the *E. coli* clones containing pPL212, pPL216, PPL517 and pBR322 were prepared from overnight cultures grown in NY medium supplemented with tetracycline. Cells were concentrated 10-fold in 100 mM phosphate buffer, pH 7.0. DNase was added and the cells were ruptured by passing them twice through a French Press (12000 lb/in). The extracts were centrifuged for 60 min. at 40000× g and the supernatants were assayed for cellulase activity. The cell-free extract of *E. coli* MC1000(pPL212), *E. coli* MC1000 (pPL517) and *E. coli* MC1000 (pPL216) contained 8 units, 7.2 units and 0.2 units respectively of cellulase/ml of original culture volume. (FIG. 2). 1/7 of the total cellulase activity in these cultures was found in the supernatant. The *E. coli* MC1000(pBR322) clone showed no cellulase activity.

The high level of cellulase activity in extracts of strains carrying the plasmids pPL212 and pPL517 is most likely due to an increased transcription of the cellulase gene originating from the β-lactamase promoter on pBR322. It was concluded that the cellulase is expressed in the direction shown in FIG. 2.

Measurements of the viscosity of a CMC solution and of the release of reducing sugars indicated that the cloned cellulase is an endo-(1,4)-β-glucanase.

Maxicell and zymogram analysis

The molecular weight of the endoglucanase protein was analyzed by the maxicell technique. The plasmids pPL212, pPL216 and pBR322 were transformed into the maxicell strain CSR603 (Sancar et al., 1979) to analyze for plasmid-encoded proteins. The plasmid pPL212 gave rise to three polypeptides of 75000 D, 65000 D and 58000 D in addition to the proteins encoded by pBR322. Apart from the pBR322 proteins, no proteins encoded by the plasmid pPL216 could be detected, due to the low expression of the cellulase gene. The three polypeptides from pPL212 were tested for cellulase activity using a gel replica technique, (Beguin, 1983).

A comparison of the cellulase activity bands and the bands on the autoradiogram from the polyacrylamide gel showed that the 75000 D and at least one of the 58000 and 65000 D protein bands had cellulase activity. It was also found the supernatant of the Bacillus spp. PL236 culture contained at least three different proteins with cellulase activity. One of these proteins comigrated with the 58000 D protein synthesized in the maxicell. Cell extracts from *E. coli* MC1000 (pPL212) only revealed one active band comigrating with the 58000 protein from the maxicell *E. coli* CSR603 (pPL212). As mentioned previously, the following sequence data showed that the plasmids pPL212 and pPL216 did not contain the entire Endo1 endoglucanase gene. The 75000 D active protein seen in the maxicell *E. coli* CSR603 (pPL212) is thus a fusion protein, where 105 C-terminal amino acids are encoded by pBR322 sequences (FIG. 2). This fusion protein is apparently post-translationally processed, ending up with the 58000 D mature endoglucanase. Cell extracts from *E. coli* MC1000 (pPL217) and *E. coli* MC1000 (pPL517), which contain the complete endoglucanase gene, also gave activity bands of $M_r$ approx 58000 D and 75000 D. The 75000 D active protein from the plasmids pPL217 and pPL517, thus represents the "genuine" initial translation product from the Endo1 glucanase gene, which apparently is processed more slowly than the fusion protein from pPL212. However, both the 75000 D fusion protein synthesized from pPL212 and the "genuine" 75000 D protein synthesized from pPL517 and pPL217 are processed down to a 58000 D protein with high cellulase activity.

From the sequence data it can also be predicted that the endoglucanase expressed from pPL216 is synthesized a fusion protein, where the 26 C-terminal amino acids are encoded by pBR322 sequences (FIG. 2). This protein was not detected by the maxicell technique and zymograms using extract from PL216 only revealed one active band of 58000 D, which most likely represents the processed protein. The processing in *E. coli* of the two fusion proteins from pPL212 and pPL216, which represent two different lengths of the C-terminal "tail" thus results, in both case, in an active protein of approx. 58000 D. This indicates that the endocellulase is processed from the C-terminal, because N-terminal processing would result in two proteins with a difference in $M_r$ of approx. 9000 D, which would easily have been detected on the zymograms.

It is therefore most likely that endoglucanase 1 (Endo1) is synthesized as a proenzyme which at least in *E. coli* (and possibly also in B.spp.) is modified by stepwise removal of approx. 150 C-terminal amino acid residues and approx. 30 N-terminal amino acid residues, corresponding to the removal of the signal peptide. The endoglucanase seems to be modified correctly as indicated by the fact that the final processing product, the 58000 D activity band present in *E. coli* MC1000 (pPL212) extract, apparently comigrate with one of the endoglucanases present in the supernatant of cultures of Bacillus spp. PL236.

Temperature optimum and stability

Figure 3:
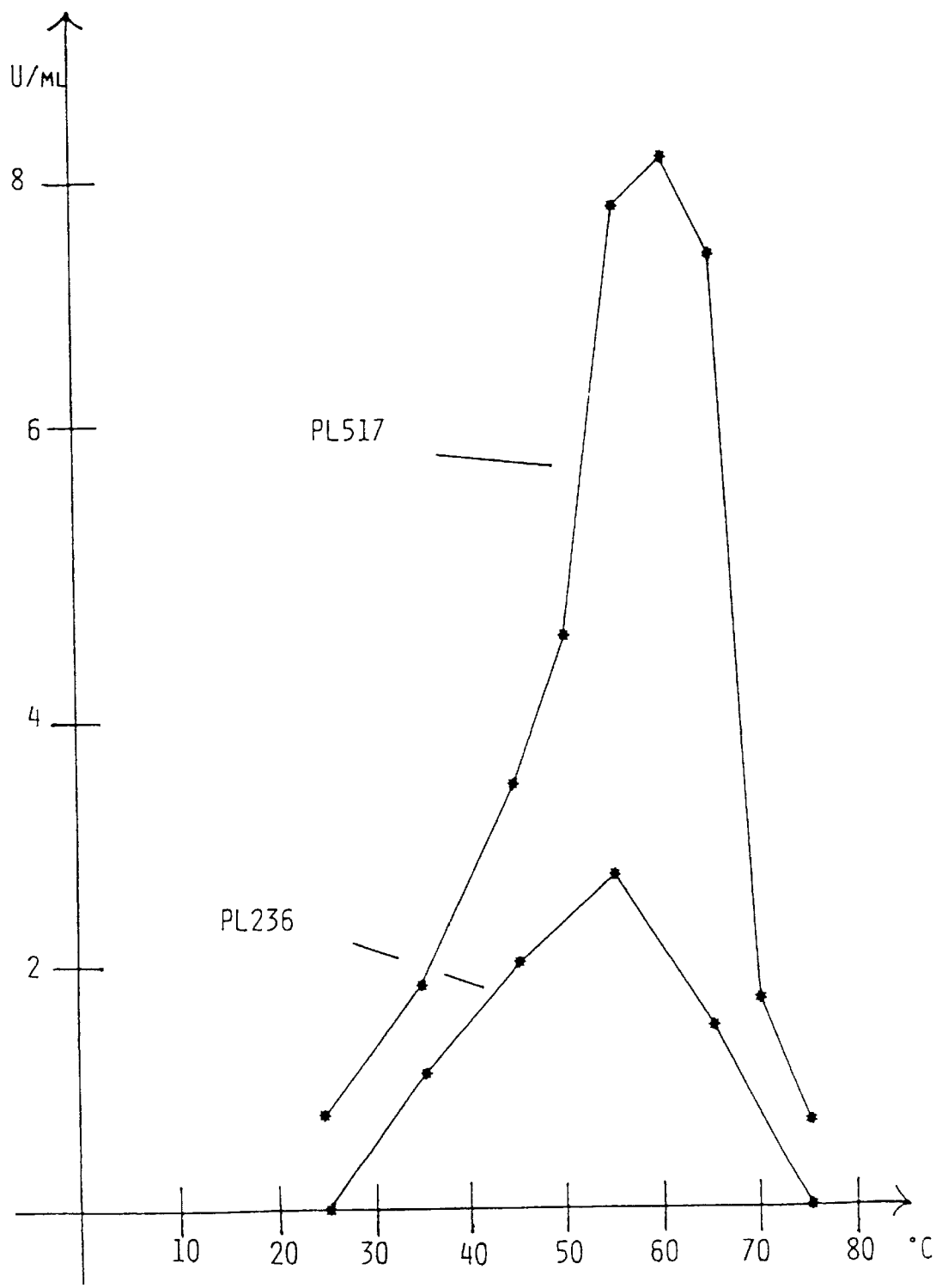
FIG. 3 Effect of temperature on the cellulase (Endo1) in extracts of E. coli MC1000 (pPL517) and on the multiple cellulase activities in the supernatant of Bacillus spp. PL236. The activity was measured at the temperature indicated after an incubation period of 30 min. See Materials and Methods. The activity at the different temperatures is presented as cellulase units/ml of the original culture volume.

The cellulase activity of the extracts was measured at different temperatures and the highest activity of Endo1 produced in *E. coli* was found at 60° C. (FIG. 3). The heat stability of the endoglucanase was tested by incubating the extracts at 50° C., 55° C. and 60° C. for varying periods and the residual activity was measured as outlined in Materials and Methods. Although the highest activity was observed at 60° C. with a fixed incubation time of 30 min., the enzyme is inactivated at this temperature with a $t_{1/2}$ of 1.2 h. At 50° C. and 55° C. no inactivation was observed after 5 h of incubation.

DNA-sequence

The nucleotide sequence of the endocellulase gene 1 (Endo1) was deduced from the plasmid pPL517 which contains approx. 2850 bp of Bacillus spp. PL236 DNA.

Figure 4:
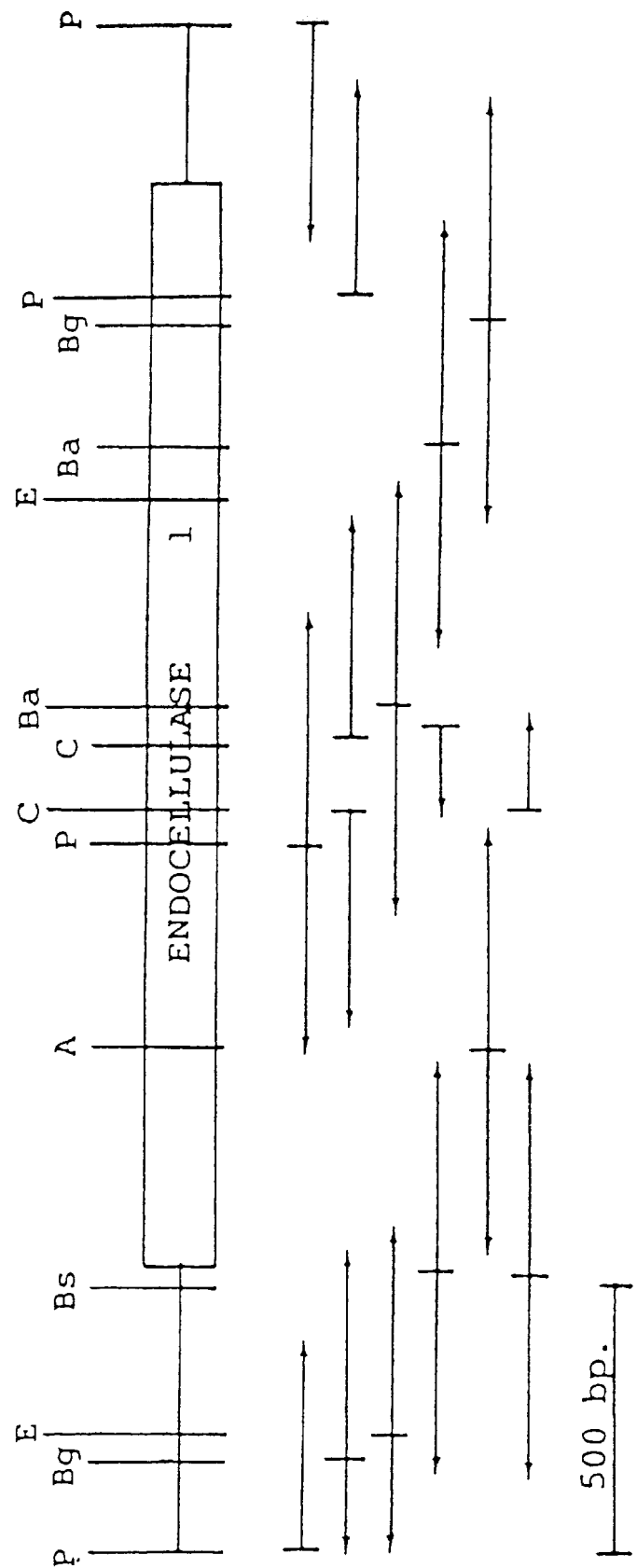
FIG. 4 Relevant restriction sites and sequencing strategy of the endoglucanase Endo1 indicated as endocellulase 1 in the figure. (↦) extent and direction of sequence reactions. Abbreviations: EcoRI (E), PstI (P), BglII (Bg), BstNI (Bs), AvaI (A), ClaI (C), BamHI (Ba).

The sequence was determined by the chemical modification method (Maxam and Gilbert, 1980) using the partial restriction map and the sequencing strategy outlined in FIG. 4.

The complete nucleotide sequence is shown in Sequence listing ID#1. A computer analysis of this sequence revealed only one open reading frame long enough to encode the approx. 75000 D protein detected by the maxicell and zymogram analysis of extracts from the cellulase-positive *E.* coli MC1000(pPL517). This sequence which begins at nucleotide 677 and ends at nucleotide 2776, encodes an enzyme of 700 amino acids. The $M_r$ calculated from the DNA sequence was 77006 D.

Within the open reading frame there were three potential initiation codons (ATG at positions 677, 737 and 749), but only the ATG codon at position 677 was preceded by a ribosome binding site (AAGGAGG) (Mclaughlin et al., 1981). It was therefore concluded that the ATG codon at position 677 was the correct initiation codon.

The initiation codon is followed by an amino acid sequence which resembles signal sequences found in gram-positive organisms. Such sequences consist of a relatively short hydrophilic region at the N-terminal followed by a longer sequence of hydrophobic residues.

By using the signal sequence cleavage model proposed by Heijne (1983) the cleavage site can be predicted to be between the two first alanine residues in the sequence Asn-Ala-Ala-Ala. The signal sequence is thus 31 amino acids long.

The upstream and downstream regions contained no significant homology to the consensus sequence of the sigma 43 promoter of B. subtilis and no terminator-like sequences.
Southern analysis The Bacillus spp. (PL236) chromosomal DNA was digested with HindIII, PstI, EcoRI and XhoI and plasmids pPL212 and pPL509 were used as probes for the hybridization. Plasmid pPL212 contains two PstI fragments (1350 bp. and 1000 bp.) and plasmid pPL509 contains only the 500 bp. PstI fragment of the entire Endo1 gene, represented by the plasmid pPL517, which contains three PstI fragments (1350 bp., 1000 bp. and 500 bp.) of Bacillus spp. PL236 DNA. The pPL212 probe recognized the expected two PstI fragments (1350 bp., 1000 bp.) and the pPL509 the 500 bp. PstI fragment in the Bacillus spp. PL236 PstI digest. Both the pPL212 and the pPL509 probe also recognized the same overlapping EcoRI fragment and the same overlapping HindIII fragment in Bacillus spp. PL236, EcoRI and HindIII digest. These results indicate that the Bacillus spp. PL236 DNA insert in pPL517 was cloned in a non-deleted form and that the three PstI fragments in pPL517 are continuous on the Bacillus spp. PL236 chromosome.

Expression of the Endo1 gene in B. subtilis

Figure 5:
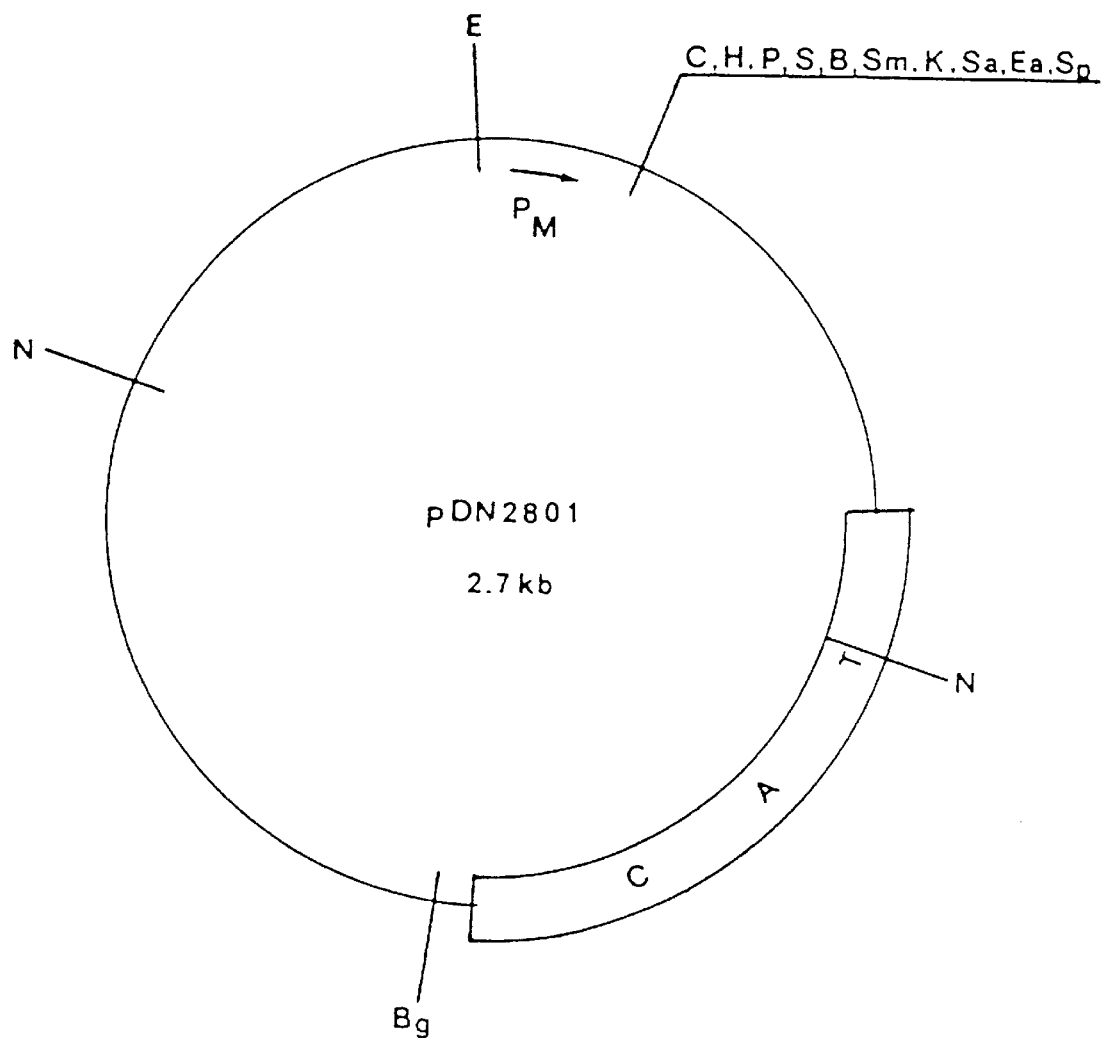
FIG. 5 is a restriction map of plasmid pDN 2801. Restriction enzyme sites are indicated as follows: EcoRI(E), BglII (Bg), HindIII (H), SmaI (Sm), SalI (Sa), SphI (Sp), PstI (P), EagI (Ea), ClaI (C), BamHI (B). CAT indicates the gene mediating chloramphenicol resistance. $P_m$ indicates the Bacillus maltogenic α-amylase promoter.

For the cloning experiments in B. subtilis, pPL517 was used as the donor of the Endo1 gene and pDN2801, carrying a strong Bacillus promoter $P_m$, was used as the Bacillus vector (FIG. 5).

The Endo1 gene-containing EagI fragment was ligated to EagI cleaved pDN2801 and by subsequent transformation to competent B. subtilis cells (DN1885), strain CH7 was obtained. To test whether the processed C-terminal part was necessary for the expression of the Endo1 gene in B. subtilis cells, a construction was made where the Endo1 gene was fused to vector sequences in the internal BglII site. This fusion replaces the coding region for the C-terminal 94 amino acids with 55 "random" amino acids encoded by vector sequences.

Similar constructions made in E. coli vectors, though fused to different vector sequences, resulted in an active periplasmic endoglucanase in E. coli, which was processed in the "correct" manner. Part of the Endo1 gene contained in the BglII fragment from pPL517 was ligated with BamHI cleaved pDN2801 and subsequent transformation to competent B. subtilis cells (DN1885) resulted in strain CH14.

Figure 6:
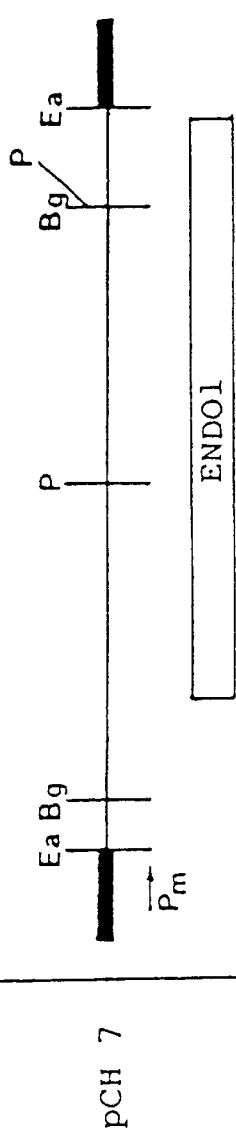
FIG. 6 Restriction maps of different plasmids (B. subtilis replication origin) carrying the Endo1 gene. The maltogenic alpha-amylase promoter is indicated by the arrow ($P_m$), which also indicates the direction of the transcription of the Endo1 gene; (▬): pDN2801, (■): tail of PDN2801 encoded sequences. Restriction enzyme sites are indicated as follows: EagI (Ea), BglII (Bg), PstI (P), BamHI (B). The endocellulase activity in extracts of B. subtilis DN 1815 containing the indicated plasmids is shown to the right (A) as endoglucanase units/ml culture medium.

Transformants were in both cases screened for their chloramphenicol resistance, and the desired plasmid constructions in the strains CH7 and CH14 by restriction analysis of their plasmids. The two versions of the Endo1 gene on the plasmids pCH7 and pCH14 are thus transcribed from the same promoter $P_m$. A restriction map of the plasmids is shown in FIG. 6.

The B. subtilis DN1885 used for these experiments produces an endoglucanase of its own, which of course gave some background activity. The Endo1 gene product was exported to the culture medium from the recombinant strain CH7, and the activity measured in the culture supernatant was approximately 20 times higher than the background activity (FIG. 6). No extracellular activity above the background level was detected from the recombinant strain CH14 which contains the Endo1 gene with the substituted C-terminal.

The culture supernatants from the strains CH7 and CH14 and cell extract from CH7 cells were analyzed by the zymogram technique. The zymogram revealed active protein bands of approx. 75000 D and 58000 D from the CH7 cell extract and only one active protein band of approx. 58000 D from the CH7 culture supernatant. These bands correspond to those observed in E. coli and the processing of approx. 90 amino acids from the C-terminal appears to take place in B. subtilis too.

The plasmid pCH7 was transformed to PL1801, which is a derivative of DN1885 lacking the two main exoproteases (apr⁻,npr⁻), resulting in the strain CH14. The Endo1 cellulase as produced from CH14 was processed "normally" indicating that the two main exoproteases from B. subtilis are not responsible for the C-terminal processing of the Endo1 cellulase.

A very weak active band of approx. 58000 D was detected from the CH14 culture supernatant, indicating that the manipulated gene is expressed and processed in at least almost the same way as the native gene product. Among other things, the very low expression from pCH14 and the fact that the two genes are expressed from the same expression signals may indicate that the approx. 90 C-terminal amino acids are necessary for the export of the Endo1 gene product from B. subtilis.

Optimization of expression of the Endo1 gene in E. coli

In order to optimize the expression of Endo1, the Endo1 gene was combined with the strong E. coli promoters $P_R$ and $P_L$ originating from phage lambda (Remaut et al., 1981). Both promoters are repressible by the lambda cI857 repressor, which is heat labile, thus rendering the $P_R$ and $P_L$ promoters heat inducible, in cells producing the lambda CI857 gene product. (Ptashne et al., 1982).

The $P_A$ promoter is contained on the expression plasmid pPL170 together with the lambda CI857 gene. (FIG. 7; Jørgensen, 1983).

The $P_R$ promoter was placed upstream of the Endo1 gene by ligating the $P_R$ containing PvuI - SalI fragment from pPL170, to the Endo1 gene containing PvuI - SalI fragment. Transformation to competent MC1000 cells resulted in the strain TL05 containing the plasmid pTL05. In the plasmid pTL05 the β-lactamase promoter is deleted, thus bringing the Endo1 gene under transcriptional control of the $P_R$ promoter. At this point, the Endo1 gene was believed to be contained within the BglII fragment from pPL2129. The Endo1 gene fusion to vector sequences on pPL212 was therefore transferred to pTL05, resulting in a fusion protein where 105 C-terminal amino acids are encoded by vector sequences. This fusion protein is however processed correctly as shown earlier with the strain PL212. The cellulase production from TL05 is completely repressed at 28° C. and induced at 42° C.

Figure 7A:
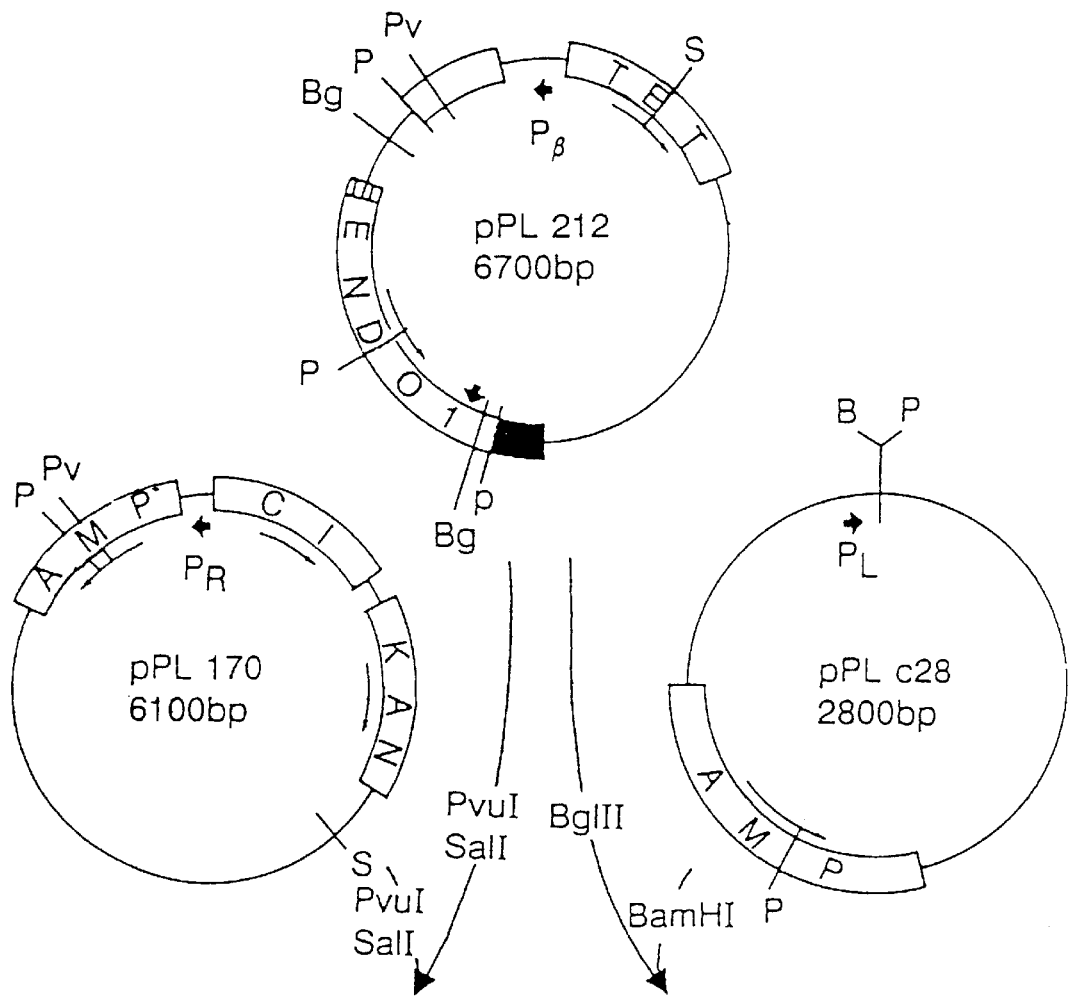
FIGS. 7a and b Construction of pTL05 and pLA03. (■): represents the C-terminal "tails" encoded by vector sequences. (↑): indicates the expected C-terminal cleavage site. Restriction sites are abbreviated as follows: PstI (P), Pvu (Pv), BamHI (B), BglII (Bg), SalI (S).
Figure 7B:
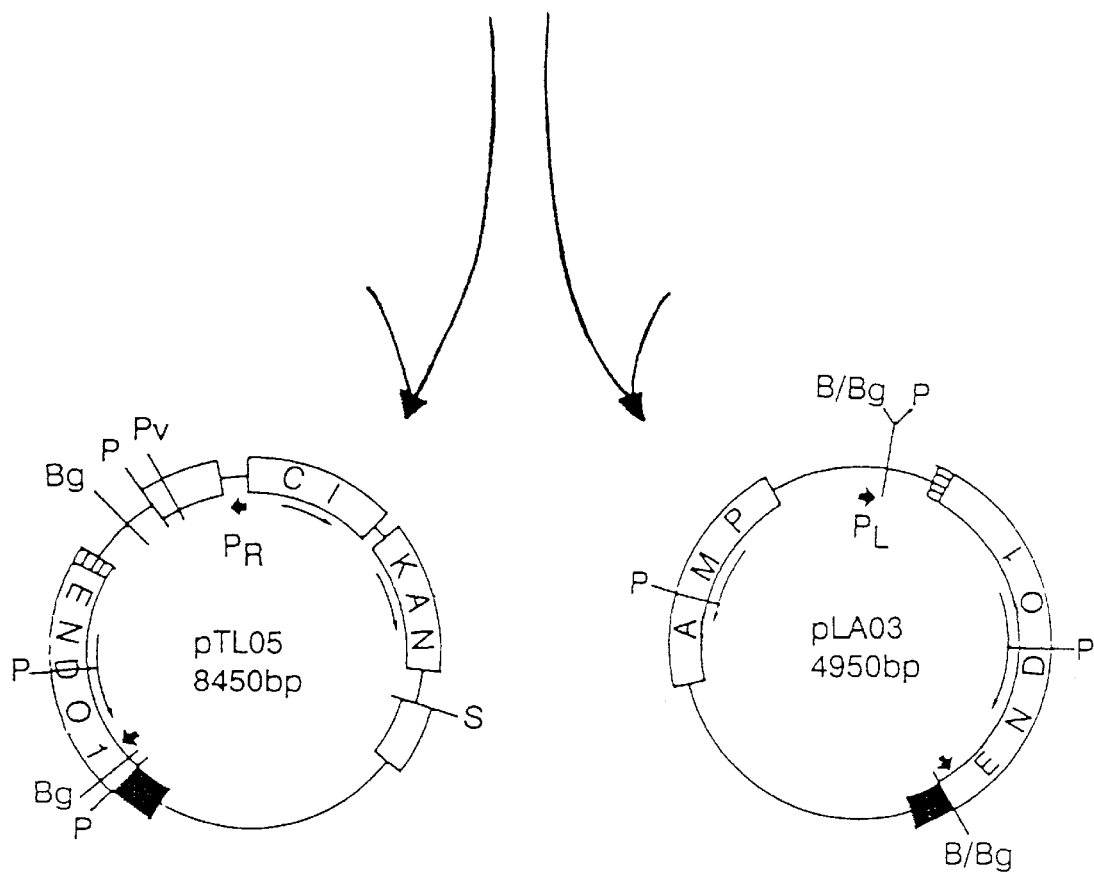

The $P_L$ promoter provided on the plasmid pPLc28 (Remaut et al., 1981) was combined with the Endo1 gene by ligating the BglII fragment from pPL212 to BamHI cleaved pPLc28. Transforming to competent PL248 cells, which are harboring the lambda cI857 gene on a compatible pACYC177 based plasmid (pNF2690), resulted in the strain LA03, containing the plasmid pLA03 (FIG. 7). The Endo1 gene is thus fused to vector sequences, but due to unspecified DNA sequences in pPLc28 the length and nature of the resulting fusion protein is unknown. The cellulase production from LA03 was completely repressed at 28° C. and induced at 40.5° C.

The cellulase production from LA03 and TL05 was evaluated at different temperatures.

LA03, TL05 and PL212 were grown overnight at 28° C. in NY medium supplemented with the appropriate antibiotics (AMP+KAN, KAN and TET, respectively). For each strain the overnight cultures were diluted 100 fold in NY medium (AMP+KAN, KAN and TET, respectively), and the diluted cultures were grown at different temperatures between 28° C. and 42° C. Cells from each culture were harvested at $OD_{450}=1$ and lysed on a French Press, and the activity in the extracts was determined as described earlier.

LA03 which exhibited the highest cellulase production was unable to grow at temperatures above 40.5° C. The experiment was repeated without antibiotic selection pressure in the diluted cultures. Similar results were obtained, but LA03 grew very slowly at temperatures above 40.5° C. However, this growth was followed by a significant loss of the plasmid pLA03. No significant loss of pLA03 at temperatures up to 40.5° C. or pPL212 and pTL05 at any temperature, was observed.

Optimization of expression of the Endo1 gene in B. subtilis

Figure 8A:
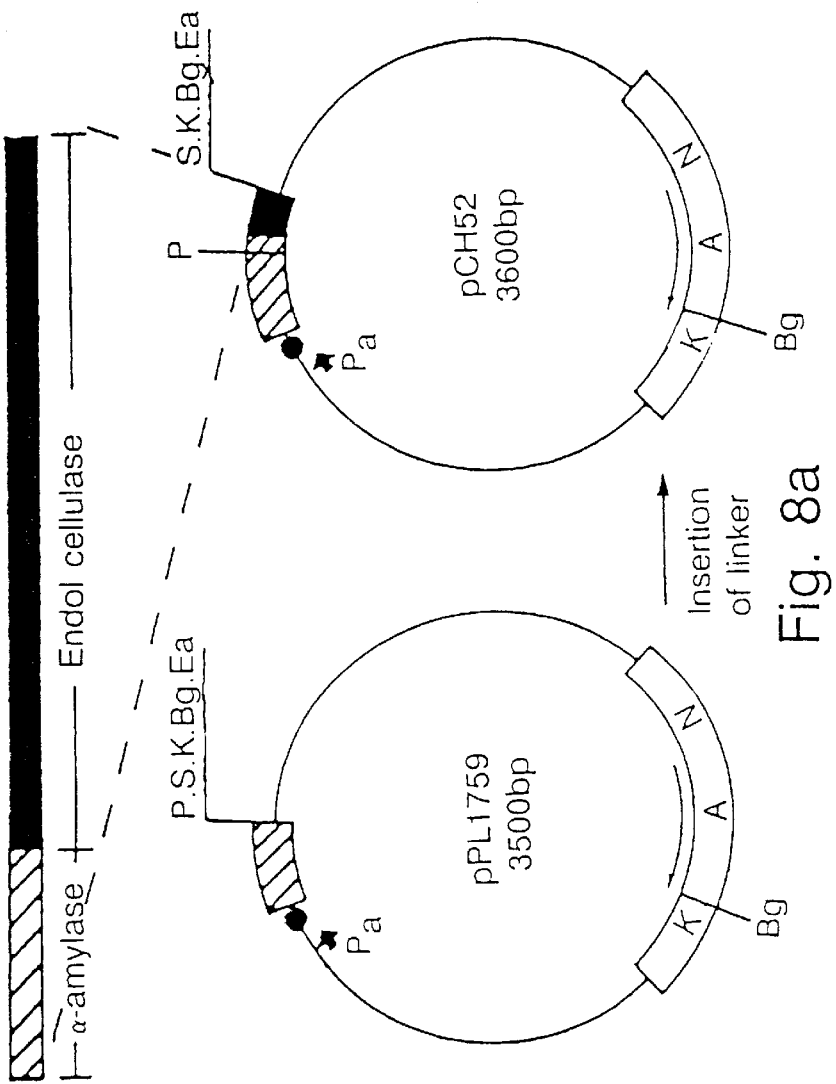
FIGS. 8a and b Construction of pCH57. (▧): Signal sequence of the alpha-amylase. (▭): signal sequence of the Endo1 glucanase (▬): "direct repeat" e.g. start of the mature Endo1 gene. (●) ribosome binding site of the alpha-amylase. (○) ribosome binding site of the Endo1 glucanase (→): alpha-amylase promoter. Restriction sites are abbreviated as follows: PstI (P); SalI (S); KpnI (K); EagI (Ea); BglII (Bg).
Figure 8B:
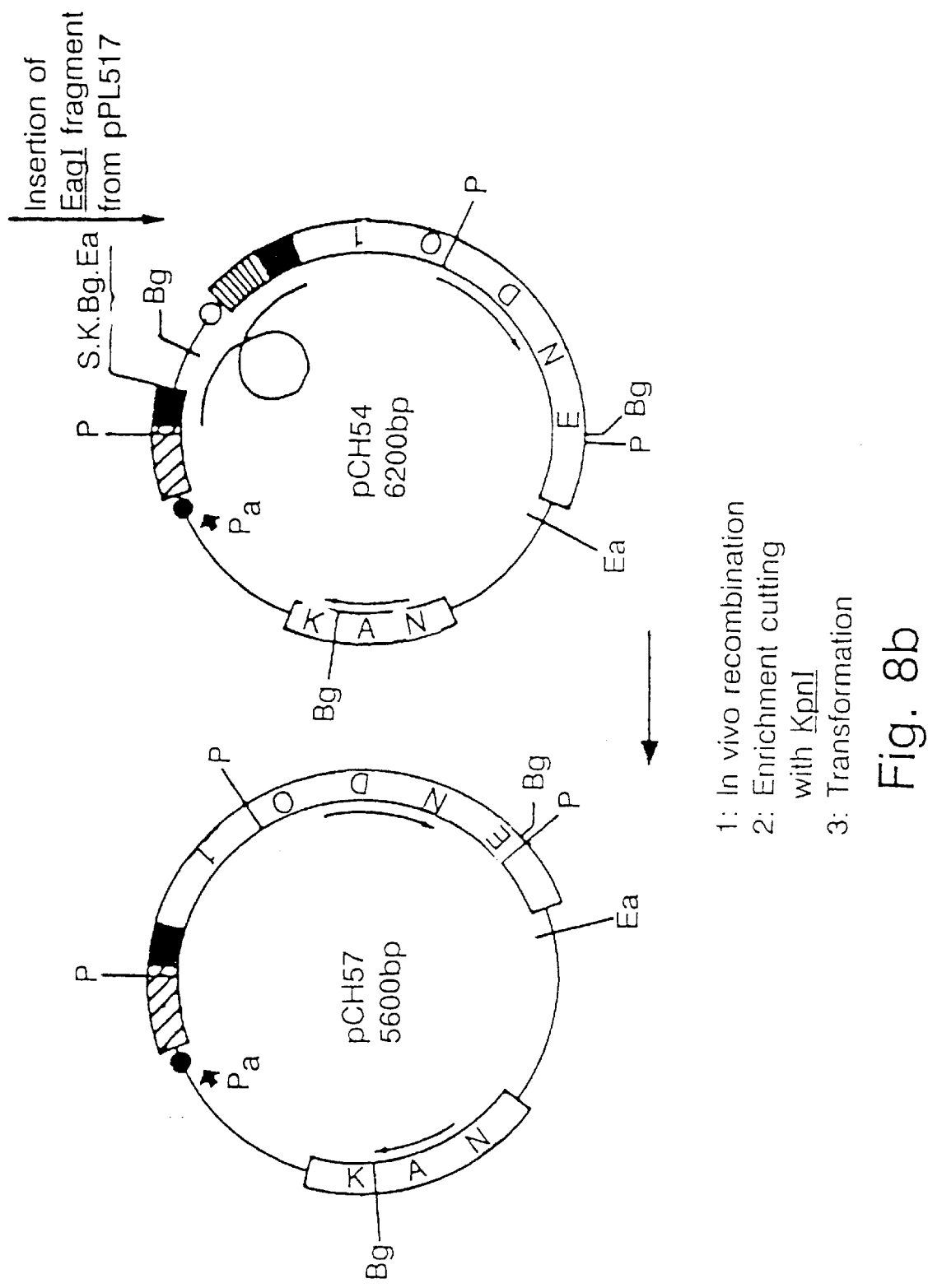

In order to optimize the expression of the Endo1 gene in B. subtilis, the Endo1 gene was fused to the expression-signals (promoter, ribosome binding site and signal sequence) from the alpha-amylase gene from B. licheniformis, which is expressed in high amounts in B. subtilis.

pPL1759 contains the promoter, ribosome binding site and most of the signal peptide of the B. licheniformis alpha-amylase (Stephens et al., 1984). The downstream side of this region ends with a PstI site, which again is followed by a polylinker (FIG. 8). Between the PstI and the SalI site in the polylinker of pPL1759, a synthetic DNA fragment consisting of two complementing oligonucleotides creating PstI and SalI "sticky" ends was inserted. In the resulting plasmid pCH52 the synthetic linker reconstitutes the missing part of the signal peptide of the alpha-amylase and further encodes the first 14 N-terminal amino acids of the mature Endo1 cellulase (FIG. 8). The linker thus creates a hybrid signal peptide cleavage site between the alpha-amylase and the cellulase. The expected cleavage site is shown in FIG. 8. From pPL517 the Endo1 gene was excised without promoter on an EagI fragment and inserted into the unique EagI site in pCH52. The plasmid in which the Endo1 gene was inserted in the correct orientation was named pCH54.

pCH54 contains two direct repeated sequences of 45 bp (e.g. the 45 N-terminal base pairs of the mature Endo1 gene) which may recombine, deleting the region between them (Ehrlich et al., 1986). This recombination event, however, occurs with a very low frequency when the repeat is as small as 45 bp. In order to enrich the amount of plasmid that has recombined, a plasmid preparation of pCH54 was cut with the enrichment restriction enzyme KpnI. pCH54 contains a unique KpnI site between the two direct repeats and only non-recombinant plasmids are cut with KpnI, while recombinant plasmids stay circular. When B. subtilis (DN 1885) was retransformed with this mixture, transformants were mostly (90%) containing recombinant plasmids, since B. subtilis competent cells are not transformed with linearized plasmid DNA. The recombinant plasmid was called pCH57 and is contained in the strain CH57. The structure was confirmed by restriction analysis, but the gene fusion was not confirmed by DNA sequencing. In this construction pCH57 the Endo1 gene is thus perfectly fused to the alpha-amylase expression signals.

The endoglucanase is produced extracellularly from the B. subtilis strain CH57, indicating that the hybrid signal cleavage site is functioning. The secreted Endo1 endoglucanase is processed to the expected $M_r$, namely 58000 D.

The production of the Endo1 cellulase from CH57 was evaluated in two different media, NY (overnight at 37° C.) and BPX (7 days at 37° C.). The BPX medium is a very rich medium in which the nutrients are slowly released, thus keeping the cells in an early stationary phase for several days during fermentation. The alpha-amylase expression signals function particularly well in this medium. The results appear from Table 1 below.

TABLE 1

| STRAIN | PLASMID | U/ml NY | U/ml BPX |
|---|---|---|---|
| CH7 | pCH7 | 6.5 | 55.0 |
| CH57 | pCH57 | 13.0 | 325.0 |
| DN1885 | — | 0.3 | 40.0 |

Analysis of the culture supernatant (BPX-medium) on PAGE revealed a dominant (90%) endoglucanase band corresponding to a concentration of endoglucanase in the supernatant of approx. 0.5 g/L.

EXAMPLE 2

Endocellulase 2 (Endo 2)

DNA-sequence

Figure 9:
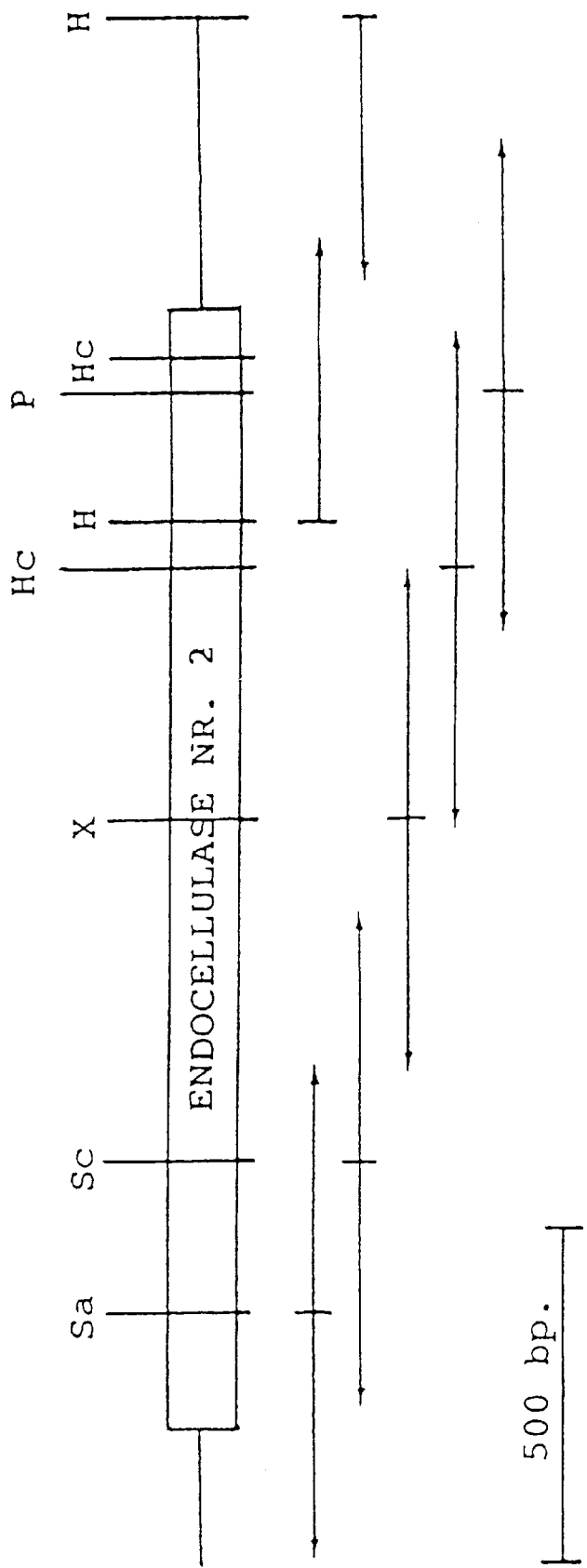
FIG. 9 Relevant restriction sites and sequencing strategy of the endoglucanase Endo2 (indicated as endocellulase 2 in the figure). (↦): extent and direction of sequence reactions. Abbreviations: ScaI (Sc), SacI (Sa), XmnI (X), HindII (Hc), HindIII (H), PstI (P).

The nucleotide sequence of endocellulase 2 (Endo2) was deduced from the plasmid pPL382 which is described above. The plasmid contains approx. 2500 bp. of Bacillus spp. PL236 DNA. The sequence was determined by the chemical modification method (Maxam and Gilbert, 1980) using the partial restriction map and the sequencing strategy outlined in FIG. 9.

The complete nucleotide sequence is shown in Sequence Listing ID#3. A computer analysis of this sequence revealed only one open reading frame long enough to encode for the approx. 56000 D protein detected in the zymogram analysis of the extract from the cellulase positive clone E. coli MC1000(pPL382). This sequence begins at position 172 and ends at 1869 and encodes an enzyme consisting of 566 amino acids. The calculated $M_r$ is 62551 D which is slightly higher than the $M_r$ of 56000 D determined by zymogram analysis. This difference could be due to inaccuracy in the zymogram analysis or to post-translational processing beyond the expected processing of the signal peptide. The ATG initiation codon in position 172 was selected because it was the only initiation codon within the open reading frame, which was proceeded by a ribosome binding site AAGGAGG (Mclaughlin et al., 1981).

This initiation codon was followed by a signal sequence-like sequence, and by use of the signal sequence cleavage model proposed by Heijne (1983), the cleavage site could be predicted to be between the two alanine residues in the middle of the sequence Leu-Ala-Ala-Ala. The signal sequence of the Endo12 is thus 30 amino acids long.

The region upstream of the open reading frame contained a sequence homologous with the sigma 43 type promoters of B. subtilis (Johnson et al., 1983) at position 46–75.

This sequence consists of TTTACA as the −35 region and TATTAT as the −10 region; the two are separated by 18 nucleotides.

A palindromic repeat sequence of 13 bp. was found downstream of the termination codon at position 1956–1981, which seems to resemble a rho-independent terminator (Rosenberg and Court, 1979).

Southern analysis

The Bacillus spp. (PL236) chromosomal DNA was digested with HindIII, PstI, EcoRI and XhoI and the plasmid pPL382 was used as a probe for the hybridization. The hybridization pattern obtained confirmed that the Bacillus spp. PL236 DNA was cloned in non-deleted form, that the two HindIII fragments from pPL382 was continuous on the Bacillus spp. PL236 chromosome and that the Endo2 gene was different from the other cloned endoglucanases.

Expression of Endo2 in B. subtilis

Plasmid pPL382 was transformed to B. subtilis DN1885 to achieve secretion of the mature Endo2 product. B. subtilis DN1885 (pPL382) was grown aerobically in 640 ml LB-medium containing 10 μg/ml tetracycline for 30 hours. The supernatant was concentrated by precipitation for 24 hours with $(NH_4)_2SO_4$ at 70% saturation. After 5 hours of dialysis against 100 mM Tris-HCl pH 7, the concentrated supernatant was heated to 55° C. for 15 minutes. Denatured protein was removed by centrifugation and the soluble proteins were subsequently precipitated with $(NH_4)_2SO_4$ at 70% saturation. The resolubilized proteins were dialyzed against 100 nM Tris-HCl pH 7 with a final volume of 2 ml and were applied to a 80 cm×1 cm gel filtration column containing Ultrogel AcA 44 (LKB). Active fractions were pooled, concentrated and applied to a SDS containing polyacrylamide gel, where the endoglucanase appeared as a single band at 56 kDa. The activity yield of the method was approximately 10%.

The endoglucanase comigrates with the endoglucanase obtained from extracts of MC1000 (pPL382) as detected by Zymogram analysis in the supernatant of DN1885 (pPL382). The endoglucanase activity of DN1885 (pPL382) is about 25 times that of strain DN1885 when grown in NY medium.

EXAMPLE 3

Endocellulase 3

Physical mapping of the endocellulase clone 3

Figure 10:
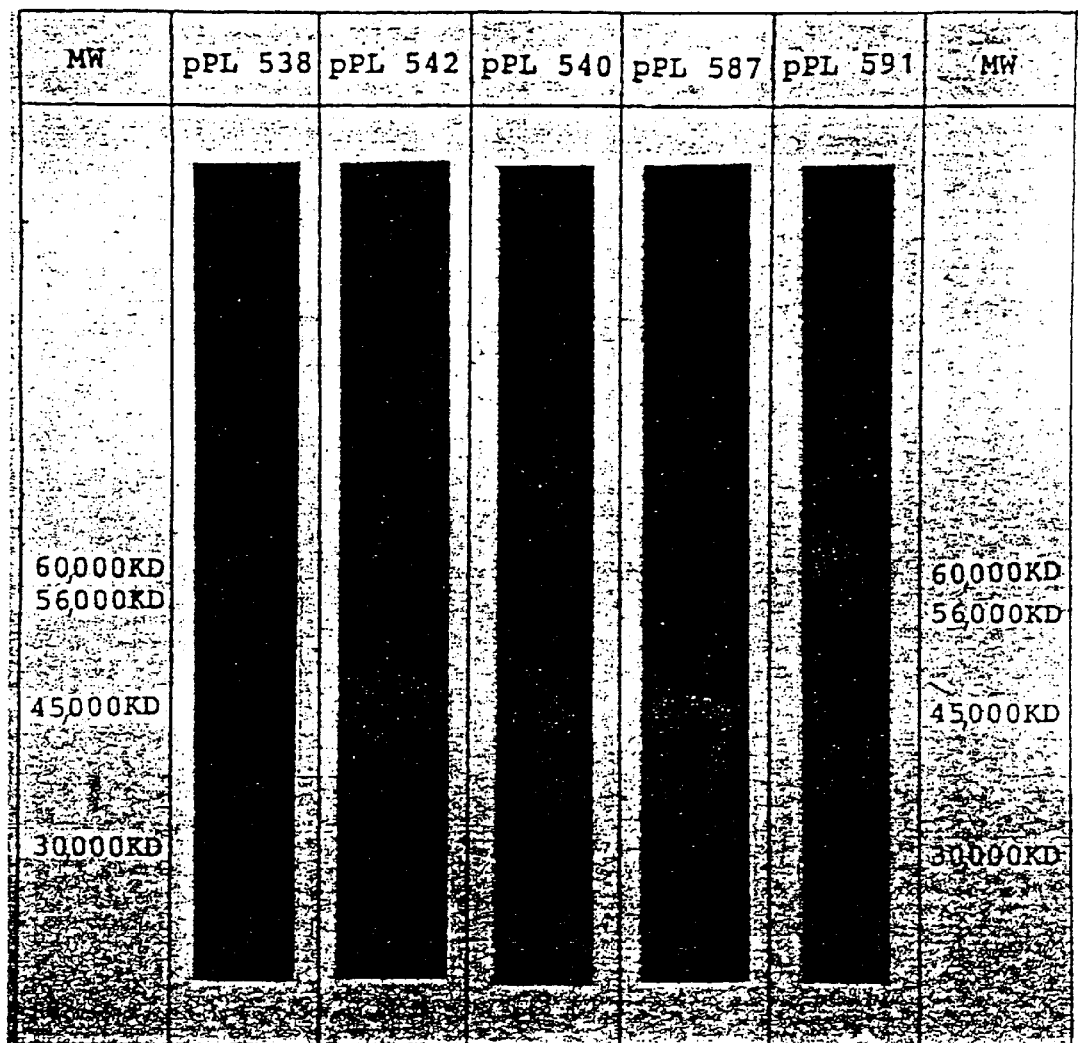
FIG. 10 Zymogram showing the molecular weight of the active proteins resulting from different plasmids carrying the original endoglucanase 3 clone (pPL591) as well as deletions in the original insert.

The endocellulase clone 3 is represented by the plasmid pPL591 which contains a 11000 bp. EcoRI fragment of Bacillus spp. PL236 DNA. A partial restriction map of this plasmid is shown in FIG. 10. Zymogram analysis of extracts from E. coli MC1000(pPL591) shows that the insert gives rise to four proteins with cellulase activity. The approx. $M_r$ of these proteins were 60000 D, 56000 D, 45000 D and 30000 D (FIG. 10).

Southern analysis showed that the EcoRI fragment from pPL591 was cloned in a non-deleted form from the Bacillus spp. PL236 chromosome, and indicates that the DNA did not contain the DNA-sequences encoding the Endo1 and Endo2 genes.

Figure 11:
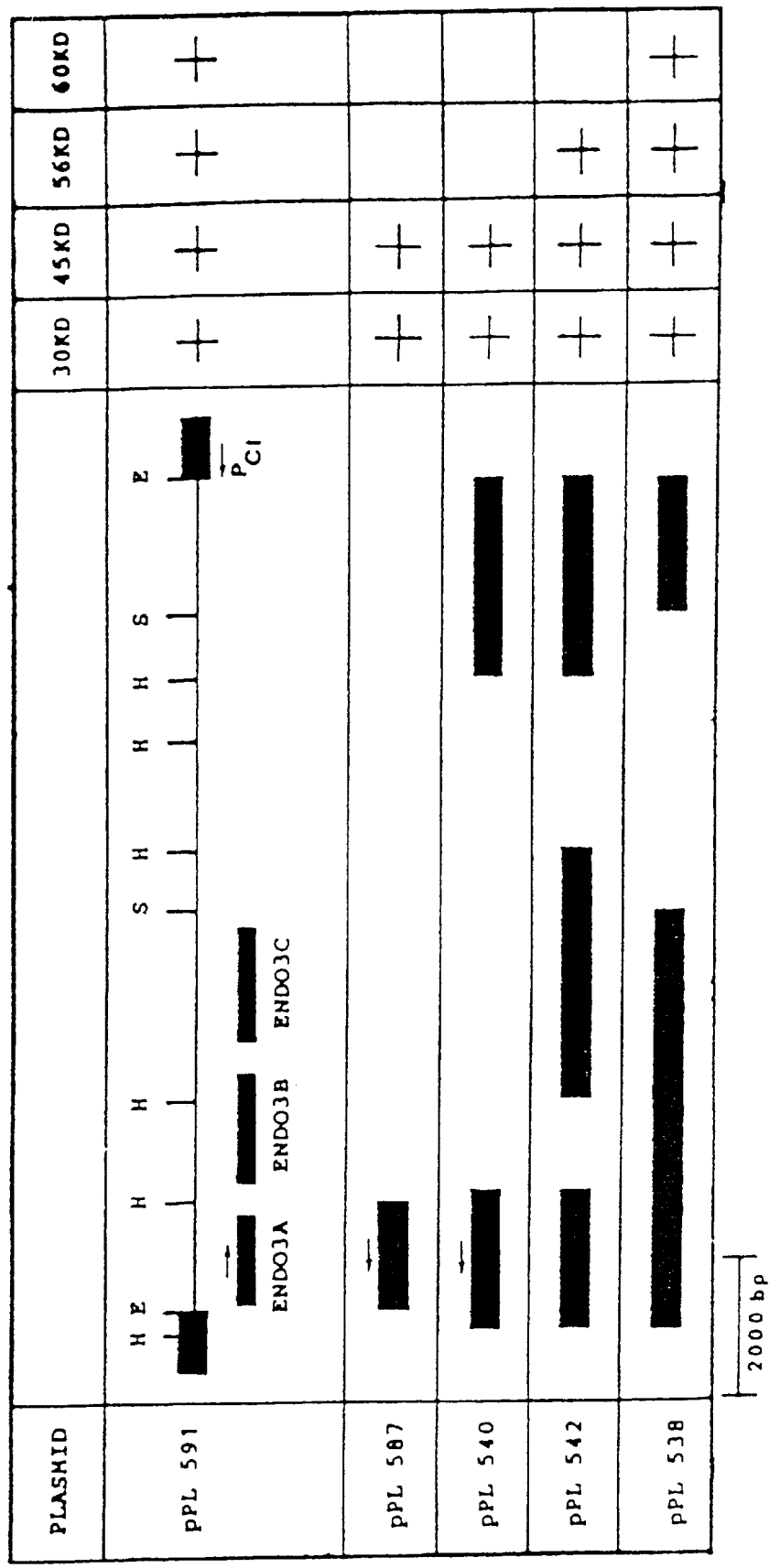
FIG. 11 Restriction maps of the endoglucanase 3 clone (indicated in the figure as endocellulase 3) (pPL591) and plasmids containing deletions in the original insert. The position of the endoglucanase genes Endo3A, Endo3B and Endo3C, on the insert in plasmid pPL591 predicted from the data shown in the zymogram (FIG. 10) is shown on the restriction map. Restriction enzyme sites are indicated as follows: HindIII (H), SmaI (S), EcoRI (E).

To analyze whether these proteins represented post-translational processing products from one or several cellulase genes, deletion plasmids were made using the restriction enzymes HindIII and SmaI. Deletion of the 4800 bp. SmaI fragment, resulting in the plasmid pPL538, did not eliminate any of the four cellulase bands on the zymogram. The B.spp. DNA insert on pPL591 contained 5 HindIII sites. Digestion of pPL591 with HindIII thus gave 6 fragments of 6600 bp. (vector fragment), 3200 bp., 1700 bp., 1550 bp., 1350 bp. and 900 bp., where the 1700 bp. fragment had originated from the HindIII site within the pUN121 vector plasmid (FIG. 11).

Elimination of all of the HindIII fragments except the 1700 bp. fragment (reinserted in the opposite direction) resulted in the plasmid pPL540. Removal of the rest of the Bacillus spp. PL236 DNA by eliminating the EcoRI fragment from pPL540 resulted in the plasmid pPL587. Both the E. coli MC1000(pPL540) and the E. coli MC1000(pPL587) were cellulase-positive and zymogram analysis of extracts from these clones revealed only the 45000 D and 30000 D proteins. The protein-coding capacity of the Bacillus spp. PL236 DNA (approx. 1500 bp.) is approx. 55000 D, which is too small to contain two endoglucanase genes of 45000 D and 30000 D. The 30000 D protein on the zymogram is thus most likely a result of immature post-translational processing of the 45000 D protein. The cellulase gene encoding the 45000 D protein was designated Endo3A. The Endo3A gene was cloned in both directions on the plasmids pPL587 and pPL538 giving rise to the same two proteins, thus eliminating the chance of the protein being a fusion protein.

Elimination of the 1550 bp., the 1350 bp. and the 900 bp. fragment resulted in the plasmid pPL542. Extracts from E. coli MC1000(pPL542) revealed cellulase positive proteins of approx. 30000 D, 45000 D, 49000 D and 56000 D (FIG. 10). From these preliminary results, the existence of two additional endoglucanase genes within the original insert on pPL591 and pPL538 are postulated. The additional endoglucanase genes are designated Endo3B and Endo3C. Their postulated position on the Bacillus spp. PL236 DNA is shown in FIG. 11. The postulated model is based on the assumption that the 60000 D protein made from pPL538 and pPL591 is converted to a truncated fusion protein of 49000 D made from pPL542 where the HindIII fragment of 1350 bp. is deleted.

DNA-sequence of Endo3A

The DNA sequence of the Endo3A gene was deduced from the plasmid pPL540 containing approx. 1500 bp. of Bacillus spp. PL236 DNA using the dideoxy chain termination method. The gene was placed in pUC18 in both orientations, and a number of deletions were constructed. Standard primers were used except for one synthetic oligonucleotide that was used for sequencing a region with no practical restriction sites.

The C-terminal part of the gene was deduced from the plasmid pPL538. The partial DNA-sequence is shown in Sequence Listing ID#6. The sequence revealed an open reading frame coding for a protein with a $M_r$ of about 62000 D which is in agreement with the observed protein of 60 kD in the zymograms. The ATG start codon (position 30) is preceded by a typical ribosome binding site (Mclaughlin et al., 1981). The initiation codon is followed by a typical gram-positive signal sequence and by using the signal sequence cleavage model (Heijne, 1983) a signal sequence of 36 amino acids is revealed.

EXAMPLE 4

Endocellulase 4

Zymogram analysis

The endocellulase clone No. 4 is represented by the plasmid pPL592, which contains approx. 14000 bp. of Bacillus spp. PL236 DNA. A partial restriction map is shown in FIG. 1.

A zymogram analysis of extracts from E. coli MC1000 (pPL592=revealed three cellulase active proteins with $M_r$ values of approx. 92000 D, 74000 D and 71000 D. Further analysis is necessary to determine whether these proteins are encoded by one or several cellulase genes.

Southern analysis confirmed the origin of the cloned DNA on the Bacillus spp. PL236 chromosome, and indicates that the cloned DNA is not represented on the other endoglucanase clones.

EXAMPLE 5

A. Endo1 cloned and expressed in *Bacillus subtilis*

An agar slant was inoculated with *B. subtilis* strain CH 57 and incubated for 20 hours at 37° C. 10 ml of a 0.9% NaCl-solution was added to the test tube which was shaken to suspend the cells. The cell suspension was used to inoculate a 2 l fermentor.

The following parameters were used to run the fermentation:
Temperature: 37° C.
Aeration: 1.1 l/minute.
Stirring: 1100 rpm.
Fermentor: A 2 l model with a working volume of 1.5 l.

The pH was maintained between 6.2 and 7.2 for the first 40 hours of fermentation. After that the pH was maintained between 6.7 and 7.2. The pH was maintained within this range by dosing with $NH_3$ and $H_3PO_4$.

Dosing of a glucose solution was initiated after 40 hours at a flow rate of 3.7 ml/hour.

| Substrate | |
|---|---|
| Potato starch degraded with Termamyl* | 50 g |
| Soybean meal | 110 g |
| Corn steep Liquor | 16.5 g |
| Alburex (potato protein) | 27.5 g |
| $(NH_4)_2SO_4$ | 2.2 g |
| $KH_2PO_4$ | 1,2 g |
| $Na_2HPO_4 \cdot 2H_2O$ | 5,9 g |
| Water added up to 1100 ml. | |
| *Termamyl is a commercial *B. licheniformis* α-amylase available from Novo Nordisk A/S. | |
| Glucose solution | |
| Glucose · $H_2O$ | 600 g |
| Citric acid | 0,6 g |
| Water added up to 1000 ml | |

The fermentation was stopped after 166 hours of fermentation at an $OD_{650}$ value of 122. At that time there were 1200 ml of fermentation broth in the fermentor.

The fermentation broth was centrifuged, and the extracellular volume was 400 ml containing 40 CMC-endoase units per ml (16.000 CMC-endoase units in all). The culture medium was further processed by filtration and dilution followed by concentration on an Amicon ultrafiltration module with a cut-off at 10.000 MW. The concentrated enzyme solution was frozen.

Half of the frozen liquid was thawed and diluted with deionized water and then concentrated once more on an Amicon ultrafiltration module. The total yield was 4471 CMC-endoase units (from 8000 CMC-endoase units).

The total volume of 1050 ml was subjected to ion exchange chromatography at pH 7. The enzyme was bound to a DEAE-Sephacryl anion exchange column (300 ml volume) at pH 7 (50 mM tris-HCl). The Endo1 enzyme was eluted at pH 7 with 0.3 M NaCl.

The purified enzyme has a molecular weight of 58,000 D on SDS-PAGE. The pI is 4.0. Its activity is 30 CMC-endoase units per mg protein.

The protein determination is based on the amino acid composition of the enzyme deduced from the DNA sequence: 13 tryptophan, 30 tyrosine and a molecular weight of 57,566 D. The extinction coefficient is calculated by means of the following formula:

$$(13 \times 5559 + 30 \times 1197)/57566 = 1.88$$

The purified enzyme has an endoglucanase activity of 57 CMC-endoase units per ml and an absorbance at 280 nm of 3.6. Thus, $(57 \times 1.88)/3.6 = 30$ CMC-endoase units per mg protein.

B. Stability of Endo1 in detergents

The following 4 detergent compositions were used:

1. USA liquid detergent: 2 gram per liter of 6° hardness water (1 part tap water to 2 parts deionized water). The pH was measured to 7.29.
2. USA Heavy Duty Powder detergent: 0.9 gram per liter of 6° hardness water. The pH was measured to 9.2.
3. Heavy Duty Powder detergent (2) with bleach and activator: 0.12 gram/l Na-perborate tetrahydrate and 0.088 gram/l NOBS. The pH was measured to 9,2.
4. European Heavy Duty Powder detergent with bleach and activator (Batch DR 8806 Europe). 5 gram per liter in 9° hardness water.

Celluzyme™ (batch CAX 007 crude enzyme with cellulase and other enzymes) 2353 CMC-endoase units per gram was compared with Endo1 30000 CMC-endoase units per gram.

The enzymes were diluted to 3 CMC-endoase units per ml in all 4 detergent solutions: The endoglucanase activity after dilution was measured as described above (by determining the decrease in the viscosity of CMC). The endoglucanase activity after 60 min. incubation at 40° C. was measured and compared with the initial activity. The following results were obtained:

| Detergent solution | 1 | 2 | 3 | 4 |
|---|---|---|---|---|
| Celluzyme ™ | 89% | 75% | 66% | 75% |
| Endo1 | 106% | 90% | 97% | 98% |

The standard deviation is 10%.

It appears from the table that Endo1 is more stable at a pH of 9–10 compared with Celluzyme™ in these detergents.

EXAMPLE 6

A. Preparation of full-length (~75 kD) Endo1 in *B. subtilis*

10 l of LB medium containing 1 mM $CuCl_2$ and 10 µg/ml chloramphenicol was inoculated with 10 ml of an overnight culture of *B. subtilis* DN969 (B. Diderichsen et al., *J. Bacteriol.* 172(8) 1990, pp. 4315–4321) containing the plasmid pCH7 (described above in example 1), divided among 10 sterile 2 l flasks and incubated with vigorous shaking for 36 hours at 37° C. The culture was centrifuged for 10 minutes at 10000 xg and 4° C. after which EDTA, pH 8, was added to the supernatant to a final concentration of 5 mM.

25 g of Avicel PH-105 which had been hydrated in ethanol and washed with distilled water was added to the supernatant which was left standing with gentle stirring for 2 hours at 4° C. The supernatant/Avicel mixture was centrifuged for 10 minutes at 10000×g and 4° C. The cleared supernatant was decanted off immediately after the rotor had stopped.

The Avicel/enzyme cake was resuspended and washed in 200 ml of 1 mM EDTA, and the mixture was centrifuged for 1 minute at 10000×g. This procedure was repeated twice. The Avicel/enzyme cake was then resuspended in 150 ml (1% triethylamine and 1 mM EDTA) and was left standing with vigorous stirring for 1 hour at 4° C. The mixture was centrifuged for 1 minute at 10000×g and 4° C. The supernatant was retained. This procedure was repeated twice.

The solution of enzyme and triethylamine (about 300 ml) was evaporated in vacuo to 100 ml. The temperature of the solution was not allowed to exceed 10° C. The pH was adjusted to 7 by adding 1M HCl, and the solution was frozen at −70° C.

The amount of protein in the 100 ml enzyme solution was determined to be 40 mg by means of a Bradford reagent (available from BioRad) using bovine serum albumin as the standard.

B. Characterization of the ~75 kD Endo1

The enzyme obtained above had a purity of about 90%. The enzyme was found to have a molecular weight of 75 kD on SDS-PAGE.

In immunoprecipitation experiments (carried out by rocket immunoelectrophoresis in agarose gel as described by N. Axelsen et al., Chapter 2 in *A Manual of Quantitative Immunoelectrophoresis*, Blackwell Scientific Publ. 1973), ~75 kD Endo1 was immunoreactive with a monospecific rabbit antibody raised against the core region (~58 kD form) of Endo1.

The ~75 kD and ~58 kD (processed) forms of Endo1 were tested for their ability to bind to cellulose (Avicel). 10 µg of each of ~75 kD Endo1 and ~58 kD Endo1 were added to 50 µl of a cellulose suspension (0.1% w/w Avicel, 5 mM EDTA, pH 8.0). The suspensions were shaken for 30 minutes, and the Avicel was harvested at 10000 rpm for 2 minutes. The amount of Endo1 cellulase remaining in the supernatant was analyzed by SDS-PAGE. More than 95% of the ~75 kD Endo1 was bound to the cellulose, while less than 5% of the ~58 kD Endo1 was similarly bound. This shows that the C-terminal part of the ~75 kD Endo1 cellulase comprises a cellulose-binding domain.

Extensive amino acid sequence homology was found between this region (from amino acid 554 to 700) of the Endo1 cellulase and other cellulases, e.g. an endocellulase from *Bacillus subtilis* (Nakamura et al., 1987), the middle part of the bifunctional cellulase from *Caldocellum saccharolyticum* (D. J. Saul et al., Nucl.Acids Res. 17, 1988, p. 439), two endocellulases from *Clostridium stercorarium* (W. Schwarz et al., Biotech.Lett. 11, 1989, pp. 461–466).

C. Color clarification effect of ~75 kD Endo1

The color clarification effect of ~75 kD Endo1 was determined by exposing a prewashed worn textile surface to the enzyme and then measuring the clarity of the surface color compared to the clarity of the surface color of textiles which had not been treated with the enzyme.

Black 100% cotton swatches (15×10 cm) were prewashed and tumble-dried under the following conditions Detergent: Keminus (available from Irma A/S), 1.5 g/l Temperature: 70° C.

Washing time: 60 minutes

Drying time: 30 minutes

No. prewashing/drying treatments:15

The swatches were prewashed in a conventional washing machine (Miele Deluxe Electronic W761). After each wash, the swatches were dried in a tumble-drier. The visual effect of the prewashing/drying was that the surface color turned greyish due to the presence of damaged cellulose fibers causing the worn look.

After prewashing, the swatches were washed in a Terg-O-Tometer (toploaded mini washing machine) under the following conditions Liquid volume: 800 ml Agitation: 100 movements/minute Detergent: Standard detergent, 5 g/l Washing time: 30 minutes Washing temperature: 40° C.

No. of swatches: 2

~75 kD Endo1 dosage: 0 and 60 CMC endoase units/l pH: 7.0

No. of treatments:3

Standard detergent:

LAS NANSA 1169/P: 10%

AE Berol 160: 15%

Ethanol, 96%: 10%

TEA: 5%

Water: 60%

After each wash, the swatches were rinsed in tap water and dried at room temperature.

The surface color of the swatches was analyzed by measuring reflected light. White light was projected onto the surface, and the reflection/remission was measured at 16 wavelengths (400 nm–700 nm). The results from the measurements were processed (by means of an "Elrepho 2000" apparatus available from Datacolor, Switzerland) into Hunter coordinates of which the L-coordinate represents the grey scale values. Each swatch was analyzed twice on each side, and the results shown below are a total average from the measurements of the two swatches from the same treatment. In the table, white is L=100, and black is L=0.

| Dosage | 0 CMC endoase/160 | CMC endoase/1 |
|---|---|---|
| L | 16.78 | 15.50 |
| S.D. | 0.08 | 0.03 |
| Delta L | — | 1.28 |

Comparable results were obtained with Celluzyme™ (batch PPC 2174 containing a mixture of enzymes from *Humicola insolens*, DSM 1800)

| Dosage | | | | |
|---|---|---|---|---|
| (CMC endoase/1) | 0 | 15 | 30 | 60 |
| Delta L | — | 1.02 | 1.48 | 1.90 |

REFERENCES

Beguin, P.: Detection of cellulase activity in polyacrylamide gels using Congo red-stained agar replicas. Anal. Biochem. 131 (1983) 333–336.

Bolivar, F., Rodriguez, R. L., Green, P. J., Betlach, M. C., Heyneker, H. L., Boyer, H. W. Crosa, J. H., and Falkow, S.: Construction and characterization of new cloning vehicles II. A multipurpose cloning system. Gene 2 (1977) 95–113.

Casadaban, J. M. and Cohen, S. N.: Analysis of gene control signals by DNA fusion and cloning in *Escherichia coli*. J. Mol. Biol. 138 (1980) 179–207.

Chang, A. C. Y. and Cohen, S. N. J. Bacteriol., 134, 1141. (1978).

Diderichsen, B. and Christiansen, L. Cloning of a maltogenic alpha-amylase from *Bacillus stearothermophilus*. FEMS Microbiol. lett. 56, 53–60. (1988).

Dubnau, D. and Davidoff-Adelson, R. Fate of transforming DNA following uptake by competent *B. subtilis* 1. Formation and properties of the donor recipient complex. J. Mol. Biol. 56, 209–221. (1971).

Ehrlich, S. D., Riele, H., Petit, M. A., Janniere, L., Noirot, P. and Michael, B. DNA recombination in plasmids and the chromosome of *B. subtilis*. Bacillus Mol. Genet. and Biotech.Appl. 27–33. (1986).

Heijne, G.: Patterns of amino acids near signal-sequence cleavage sites. Eur. J. Biochem. 133, 17–21 (1983).

Holmes, D. S. and Quigley, M.: A rapid boiling method for the preparation of bacterial plasmids. Anal. Biochem. 114 (1981) 193–197.

Horinouchi, S. and Weisblum, B.: Nucleotide sequence and functional map of pC194, a plasmid that specifies inducible chloramphenicol resistance. J. Bact. 150, 2, 815–825.

Johnson, W. C., Moran, C. P. Jr. and Losich, R.: (1983) Two RNA polymerase sigma factors from Bacillus subtilis discriminate between overlapping promoters for a developmentally regulated gen.

Jorgensen, P. L.: Construction of vectors for cloning of promoter. M.Sc. Thesis, The Technical University of Denmark (1983).

Keggins, K. M., Lovell, P. S. and Duvall, E. J. Molecular cloning of Bacillus DNA in Bacillus subtilis and properties of the vector plasmid pUB110. Proc.Natl.Acad.Sci.U.S.A.75, 3, 1423–1427. (1978).

Kreft, J., Burger, J. K. and Goebel, W.: Expression of antibiotic resistance genes from E. coli in Bacillus subtilis. Mol.Gen.Genet. 190: 384–389 (1983).

Laemmli, U. K.: Cleavage of structural proteins during the assembly of head of bacteriophage T4. Nature 227 (1970) 680–685.

Loening, U. E.: The fractionation of high-molecular-weight ribonucleic acid polyacrylamide gel electrophoresis. Biochem. J. 102 (1967) 251–257.

Mandel, M. and Higa, A.: Calcium dependent bacteriophage DNA infection, J. Mol. Biol. 53 (1970) 154–162.

Maniatis, T., Fritsch, E. F., and Sambrook, J.: Molecular Cloning—A Laboratory Manual. Cold Spring Harbor Laboratory, Cold Spring Harbor, N.Y., 1982.

Maxam, A. M. and Gilbert, W.: Sequencing end-labelled DNA with base-specific chemical cleavage. In: Grossman, L. and Moldave, K. (Eds., Methods in Enzymology, Vol. 65, Academic Press, New York, 1980, pp 499–560.

Mclaughlin, J. R., Murray, C. L. and Babinowitz, C. J. 1981. Unique features in the ribosome binding site sequence of the gram-positive Staphylococuccus aureus B-laclamase gene. J. Biol. Chem. 256: 11283–11291.

von Meyenburg, K., Jørgensen, B. B., Nielsen, J., and Hansen, F. G.: Promoters of the atp operon coding for the membrane bound ATP synthase of Escherichia coli mapped by Tn10 insertion mutations. Mol. Gen. Genet. 188 (1982) 240–248.

Miller, G. L.: Use of dinitrosalicyclic reagent for determination of reducing sugars, Anal. Chem. 31. (1959) 426–428.

Nakamura, A., Uozumi, T., Beppu, T. (1987). Nucleotide sequence of a cellulase gene of Bacillus subtilis. Eur. J. Biochem. 164, 317–320.

Nilsson, B., Uhlen, M., Josephson, S., Gatenbeck, S. and Philipson, L.: An improved positive selection plasmid vector constructed by oligonucleotide mediated mutagenesis. Nucleic Acids Res. 11: 8019–8030.

Ptashne, M., Johnson, A. D. and Pabo, C. O.: A genetic switch in a bacterial virus. Scientific American, November (1982).

Remaut et al., Gene 15, 1981, pp. 81–93.

Remaut, E., Stanssens, P. and Fiirs, W.: Plasmid vectors for high-efficiency expression controlled by the $P_L$ promoter of coliphage lambda. Gene, 15, 81–93. (1981).

Rigby, P. W. J., Dieckmann, M., Rhodes, C. and Berg, P. (1977): Labelling deoxyribonucleic acid to high specific activity in vitro by nick translation with DNA polymerase I. I. Mol. Biol. 113, 237–251.

Rosenberg, M. and Court, D.: Regulatory sequences involved in the promotion and termination of RNA transcription. Ann. Rev. Genet. 1979 13: 319–53.

Sancar, A., Hack, A. M., and Rupp, W. D.: Simpel methods for identifications of plasmid-coded proteins, J. Bacteriol. 137 (1979) 692–693.

Sanger, F., Nichlen, S. and Coulson, A. R. (1977). Proc. Natl. Acad. Sci. U.S.A. 74, 5463–5467.

Southern, E.: Detection of specific sequences among DNA fragments separated by gel electrophoresis. I. Mol. Biol. 98, 503–517 (1975).

Stephens, M. A., Ortlepp, S. A., Ollington, J. F. and McConnel, D. J. J.bact. Vol.158, No 1, p 369–372. (1984).

Teather, R. M. and Wood, P. J.: Use of Congo red-polysaccharide interactions in enumeration and characterization of cellulolytic bacteria from the bovine rumen. Appl. Environ. Microbiol. –3 (1982) 777–780.

Walseth, C. S.: Occurrence of cellulases in enzyme preparations from microorganisms. Tappi, Vol. 35, No. 5 (1952) 228–233.

Yanisch-Perron, C., Vieira, J. and Messing, J. Gene, 33, 103–119. (1985).

---

We claim:

1. An isolated cellulase endogenous to a strain of *Bacillus lautus* which (a) is active between about 45 and 65° C. and (b) has a pH optimum in the range of about 7.5–10.5.

2. The isolated cellulase according to claim 1 which exhibits an endoglucanase activity of at least about 10 CMC-endoase units per mg of total protein under alkaline conditions.

3. The isolated cellulase according to claim 2 which exhibits an endoglucanase activity of at least about 20 CMC-endoase units per mg of total protein under alkaline conditions.

4. The isolated cellulase according to claim 3 which exhibits an endoglucanase activity of at least about 25 CMC-endoase units per mg of total protein under alkaline conditions.

5. The isolated cellulase according to claim 4 which exhibits an endoglucanase activity of at least about 30 CMC-endoase units per mg of total protein under alkaline conditions.

6. The isolated cellulase according to claim 1 which has a molecular weight of about 45 kD.

7. The isolated cellulase according to claim 1 which has a molecular weight of about 56 kD.

8. The isolated cellulase according to claim 1 which has a molecular weight of about 60 kD.

9. The isolated cellulase according to claim 1 which has a molecular weight of about 75 kD.

10. The isolated cellulase according to claim 1 which has a molecular weight of about 92 kD.

11. An isolated DNA construct, comprising a DNA sequence encoding the cellulase according to claim 1.

12. The cellulase according to claim 1 which is in the form of a non-dusting granulate, a stabilized liquid or a protected enzyme.

13. The cellulase according to claim 12, which exhibits an endoglucanase activity of 500–10,000 CMC-endoase units per gram of the non-dusting granulate, the stabilized liquid or the protected enzyme.

14. A detergent composition comprising the cellulase according to claim 1 and a surfactant.

15. The detergent composition according to claim 14, wherein the cellulase has an endoglucanase activity of 0.3–400 CMC-endoase units per gram of detergent.

16. The detergent composition according to claim 14, further comprising one or more enzymes selected from the group consisting of protease, lipase and amylase.

17. A method of treating a cellulose-containing fabric, comprising treating the cellulose-containing fabric with the cellulase according to claim 1.

18. The method according to claim 17, wherein the treatment of the fabric with the cellulase is conducted in an aqueous medium during soaking, washing or rinsing of the fabric.

19. The method according to claim 18, wherein the aqueous medium exhibits an endoglucanase activity of more than about 250 CMC-endoase units per liter of the aqueous medium.

20. An isolated cellulase according to claim 1, wherein the strain is NCIMB 40250.

21. The isolated cellulase according to claim 20 which is encoded by the DNA sequence SEQ ID NO:1.

22. The isolated cellulase according to claim 20 which has the amino acid sequence SEQ ID NO:2.

23. The isolated cellulase according to claim 20 which is encoded by the DNA sequence SEQ ID NO:3.

24. The isolated cellulase according to claim 20 which has the amino acid sequence SEQ ID NO:4.

25. An isolated DNA construct, comprising a DNA sequence encoding the cellulase according to claim 20.

26. The isolated DNA construct according to claim 25, wherein the DNA sequence is SEQ ID NO:1.

27. The isolated DNA construct according to claim 25, wherein the DNA sequence is SEQ ID NO:3.

28. The cellulase according to claim 20 which is in the form of a non-dusting granulate, a stabilized liquid or a protected enzyme.

29. The cellulase according to claim 28, which exhibits an endoglucanase activity of 500–10,000 CMC-endoase units per gram of the non-dusting granulate, the stabilized liquid or the protected enzyme.

30. A detergent composition comprising the cellulase according to claim 20 and a surfactant.

31. The detergent composition according to claim 30, wherein the cellulase has an endoglucanase activity of 0.3–400 CMC-endoase units per gram of detergent.

32. The detergent composition according to claim 30, further comprising one or more enzymes selected from the group consisting of protease, lipase and amylase.

33. A method of treating a cellulose-containing fabric, comprising treating the cellulose-containing fabric with the cellulase according to claim 20.

34. The method according to claim 33, wherein the treatment of the fabric with the cellulase is conducted in an aqueous medium during soaking, washing or rinsing of the fabric.

35. The method according to claim 34, wherein the aqueous medium exhibits an endoglucanase activity of more than about 250 CMC-endoase units per liter of the aqueous medium.

* * * * *